US 8,674,656 B2

(12) United States Patent
Iio et al.

(10) Patent No.: US 8,674,656 B2
(45) Date of Patent: Mar. 18, 2014

(54) CARRYING CASE AND SYRINGE SYSTEM WITH SAME

(71) Applicant: Panasonic Corporation, Osaka (JP)

(72) Inventors: Toshiaki Iio, Ehime (JP); Yukihiro Takabatake, Ehime (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/783,806

(22) Filed: Mar. 4, 2013

(65) Prior Publication Data

US 2013/0175192 A1 Jul. 11, 2013

Related U.S. Application Data

(62) Division of application No. 13/128,940, filed as application No. PCT/JP2009/005135 on Oct. 2, 2009, now Pat. No. 8,398,602.

(30) Foreign Application Priority Data

Nov. 14, 2008 (JP) ................................. 2008-292793

(51) Int. Cl.
*H02J 7/00* (2006.01)
*A61M 5/32* (2006.01)

(52) U.S. Cl.
USPC ........... 320/114; 320/106; 320/107; 604/264; 604/272

(58) Field of Classification Search
USPC ........... 320/106, 107, 114, 150; 604/264, 272
See application file for complete search history.

(56) References Cited

U.S. PATENT DOCUMENTS

| 5,207,303 | A | | 5/1993 | Oswalt et al. | |
|---|---|---|---|---|---|
| 5,695,472 | A | * | 12/1997 | Wyrick | 604/136 |
| 5,731,291 | A | * | 3/1998 | Sullivan et al. | 514/23 |
| 5,848,700 | A | * | 12/1998 | Horn | 206/570 |
| 7,512,247 | B1 | | 3/2009 | Odinak et al. | |
| 7,924,562 | B2 | * | 4/2011 | Soma et al. | 361/694 |
| 2003/0040715 | A1 | | 2/2003 | D'Antonio et al. | |
| 2003/0225344 | A1 | | 12/2003 | Miller | |
| 2005/0015115 | A1 | | 1/2005 | Sullivan et al. | |
| 2005/0085799 | A1 | | 4/2005 | Luria et al. | |
| 2007/0293582 | A1 | * | 12/2007 | Hill | 514/649 |
| 2009/0194446 | A1 | | 8/2009 | Miller et al. | |
| 2010/0010561 | A1 | | 1/2010 | Go | |

FOREIGN PATENT DOCUMENTS

EP 1 418 958 5/2004
(Continued)

OTHER PUBLICATIONS

International Search Report issued Nov. 17, 2009 in International (PCT) Application No. PCT/JP2009/005135.

*Primary Examiner* — M'baye Diao
(74) *Attorney, Agent, or Firm* — Wenderoth, Lind & Ponack, L.L.P.

(57) ABSTRACT

A carrying case, which accommodates a pharmaceutical injection device for administering a pharmaceutical to a living body, comprises a case unit configured to accommodate the pharmaceutical injection device therein and a temperature regulation unit configured to regulate a temperature within the case unit. The temperature regulation unit includes: a cooling execution section configured to execute a cooling operation; a cooling fan configured to supply a cool air into the case unit; and a cooling control section configured to control the cooling execution section.

10 Claims, 30 Drawing Sheets

(56) References Cited

FOREIGN PATENT DOCUMENTS

| | | |
|---|---|---|
| JP | 3-2678 | 1/1991 |
| JP | 3-98538 | 10/1991 |
| JP | 4-332524 | 11/1992 |
| JP | 3010787 | 12/1999 |
| JP | 2001-258819 | 9/2001 |
| JP | 2005-508214 | 3/2005 |
| JP | 2005-527312 | 9/2005 |
| JP | 2007-210280 | 8/2007 |
| JP | 2007-260126 | 10/2007 |
| JP | 2008-136525 | 6/2008 |

* cited by examiner

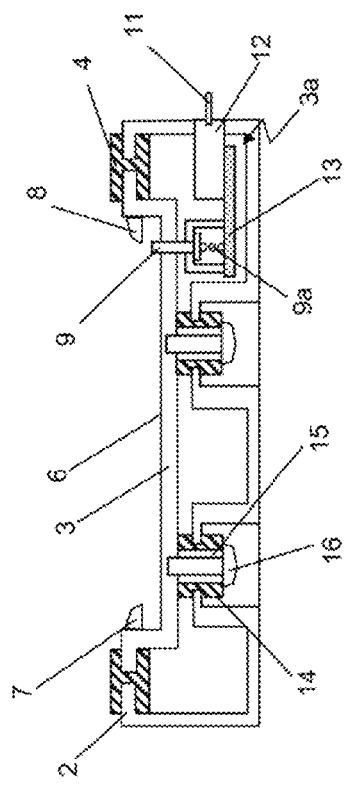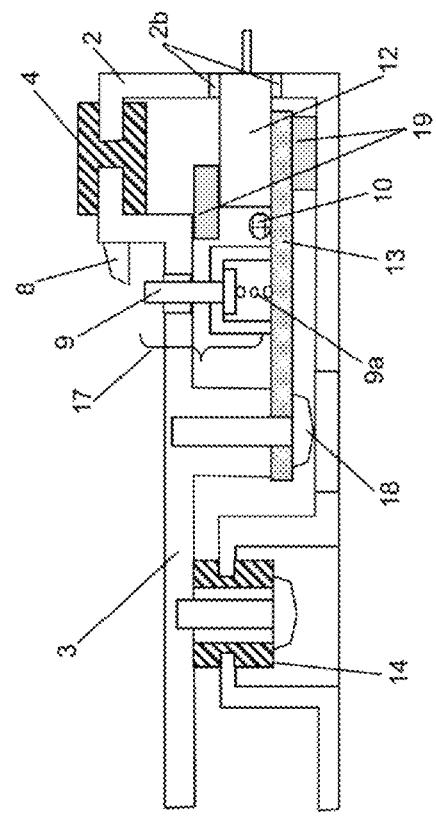
FIG. 3A
FIG. 3B

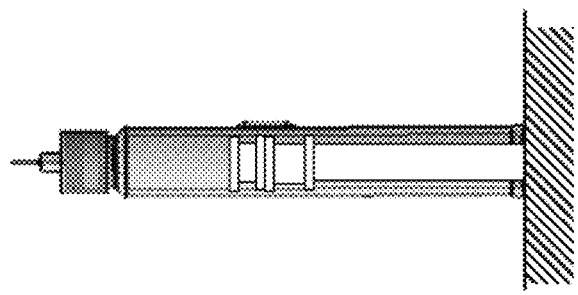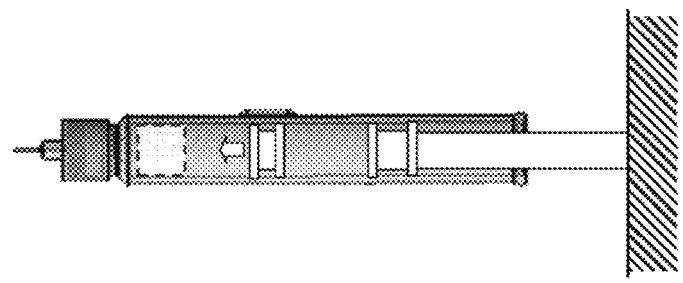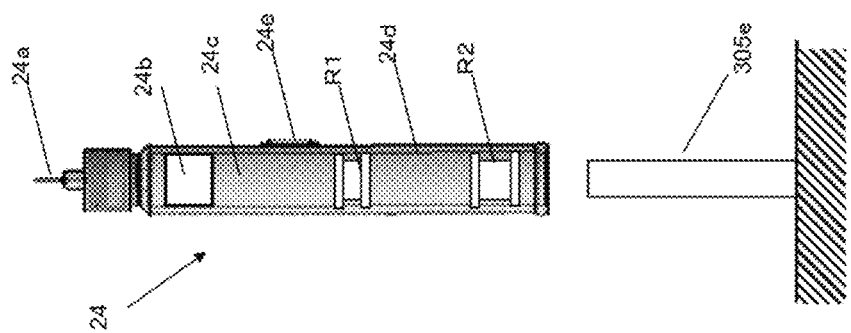

(a)

| LED TYPE | NON-ELECTRIC CHARGING | ELECTRIC CHARGING | COMPLETION OF ELECTRIC CHARGING |
|---|---|---|---|
| SINGLE-COLOR LED | LIGHTING-OUT | LIGHTING | LIGHTING-OUT |
| SINGLE-COLOR LED | LIGHTING-OUT | BLINKING | LIGHTING |
| TWO-COLOR LED | LIGHTING-OUT | LIGHTING IN RED | LIGHTING IN GREEN |

(b)

| NON-ELECTRIC CHARGING | ELECTRIC CHARGING | COMPLETION OF ELECTRIC CHARGING |
|---|---|---|
| (OPERATION SCREEN) | CHARGING | CHARGING COMPLETED |

(c)

| LED TYPE | UNCONNECTED | CONNECTED | COMMUNICATING | COMPLETION OF COMMUNICATION |
|---|---|---|---|---|
| SINGLE-COLOR LED | LIGHTING-OUT | LIGHTING | BLINKING | LIGHTING |
| TWO-COLOR LED | LIGHTING-OUT | LIGHTING IN GREEN | LIGHTING IN RED | LIGHTING IN ORANGE (BY LIGHTING IN BOTH GREEN AND RED) |

(d)

| UNCONNECTED | CONNECTED | COMMUNICATING | COMPLETION OF COMMUNICATION |
|---|---|---|---|
| NO DISPLAY | "CONNECTED TO ***" | "COMMUNICATING WITH ***" | "COMMUNICATION COMPLETED WITH ***" |

FIG. 18

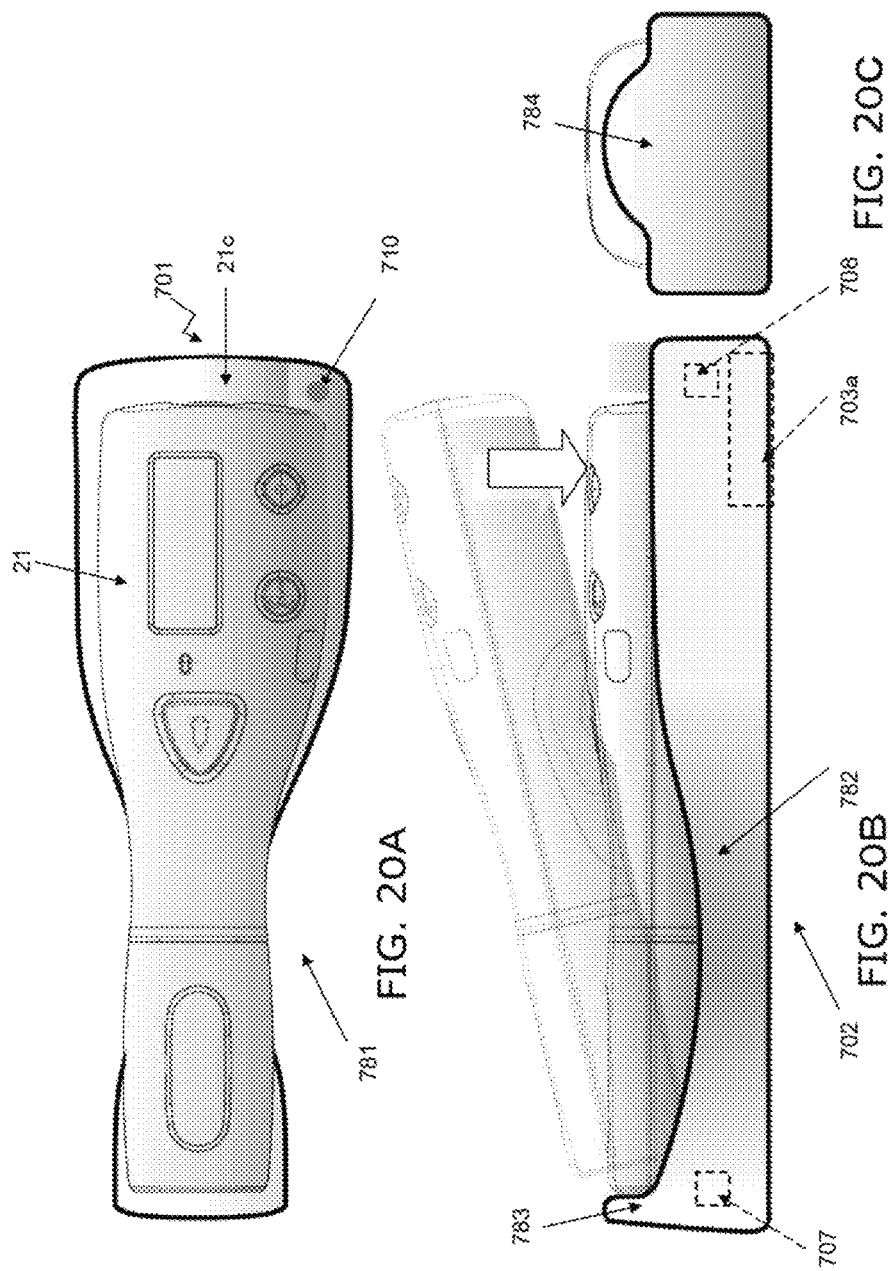

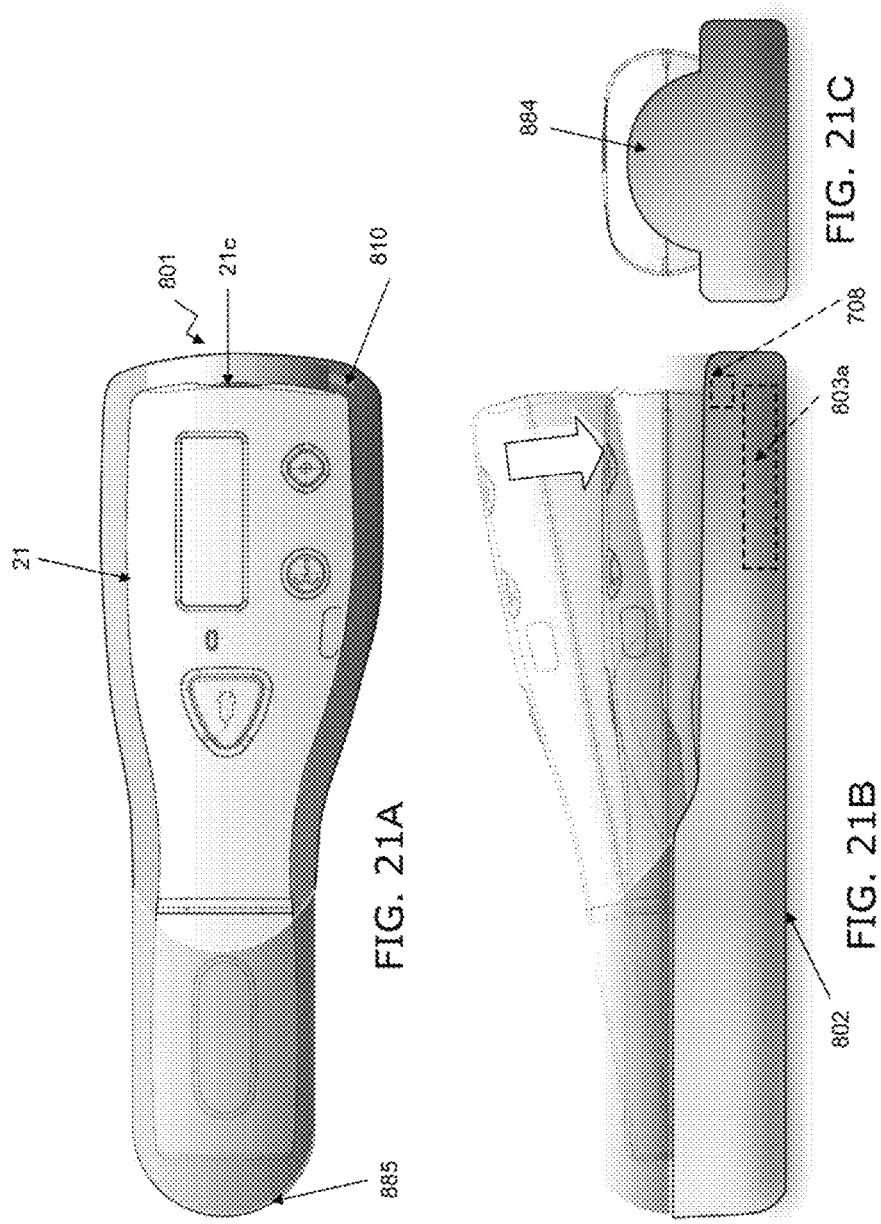

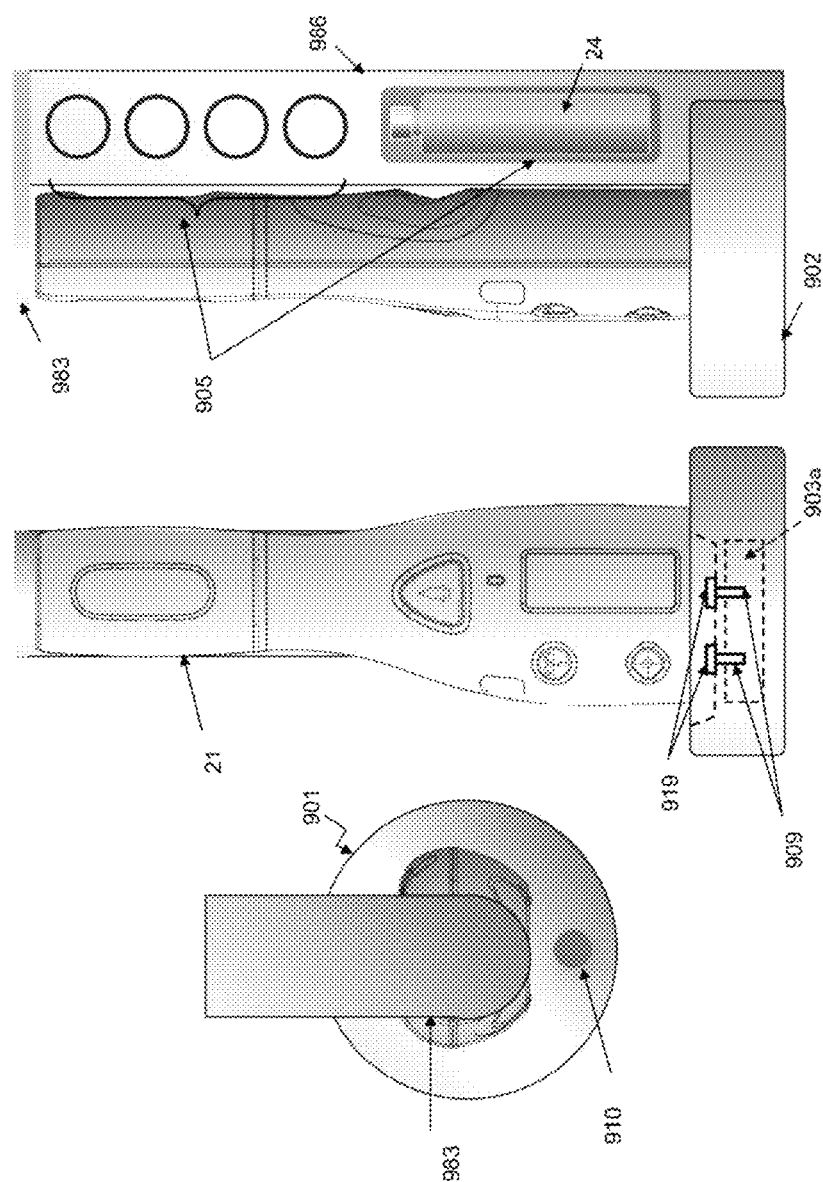

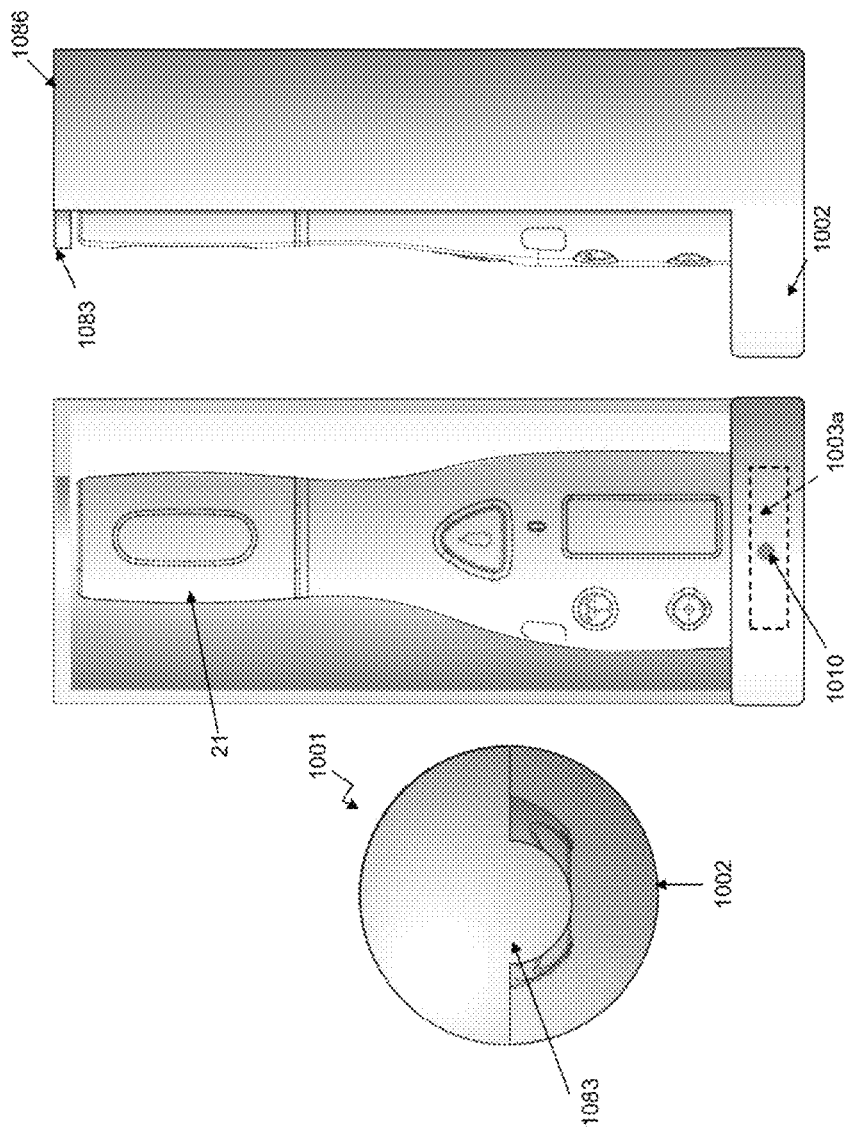

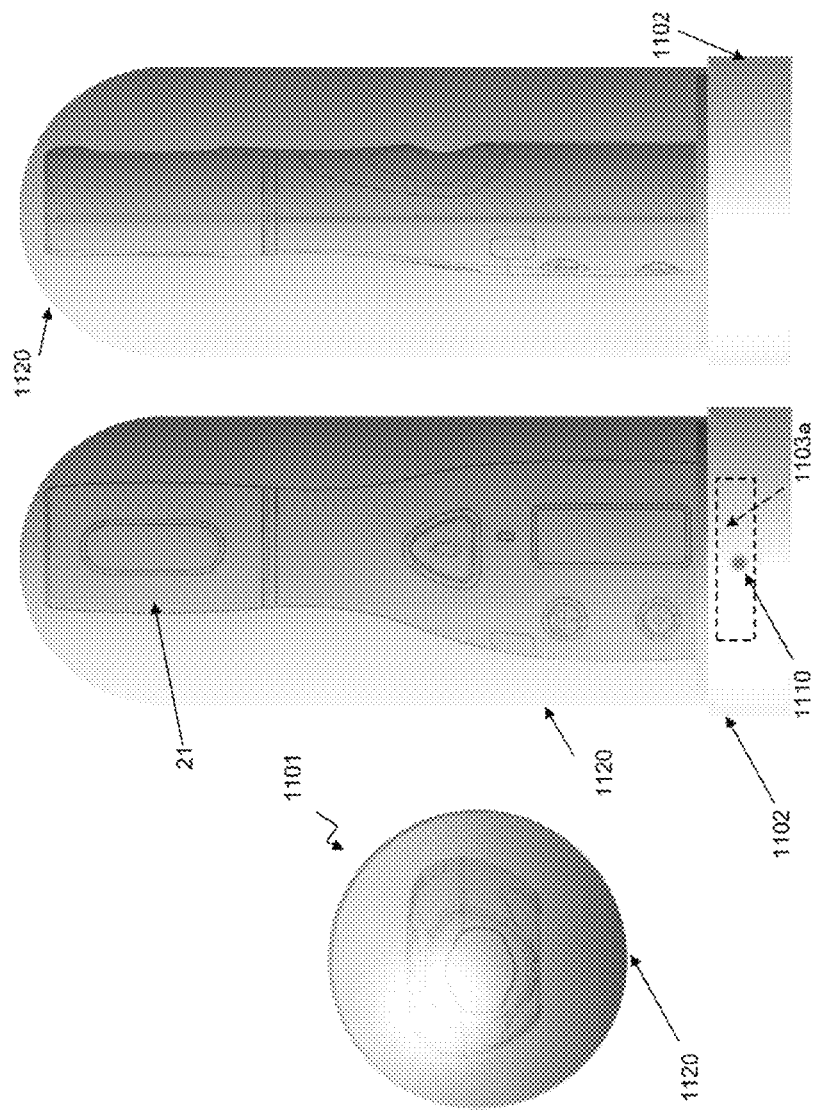

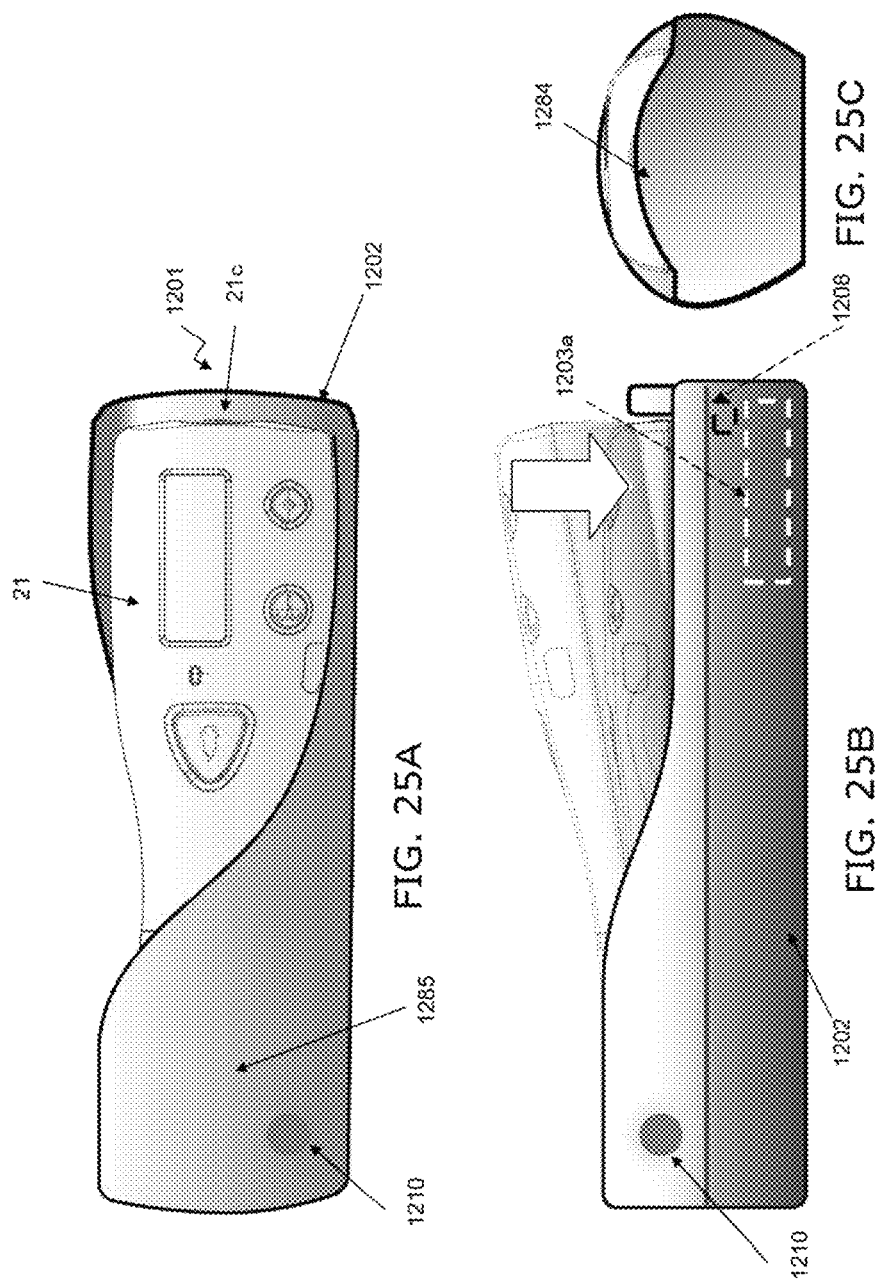

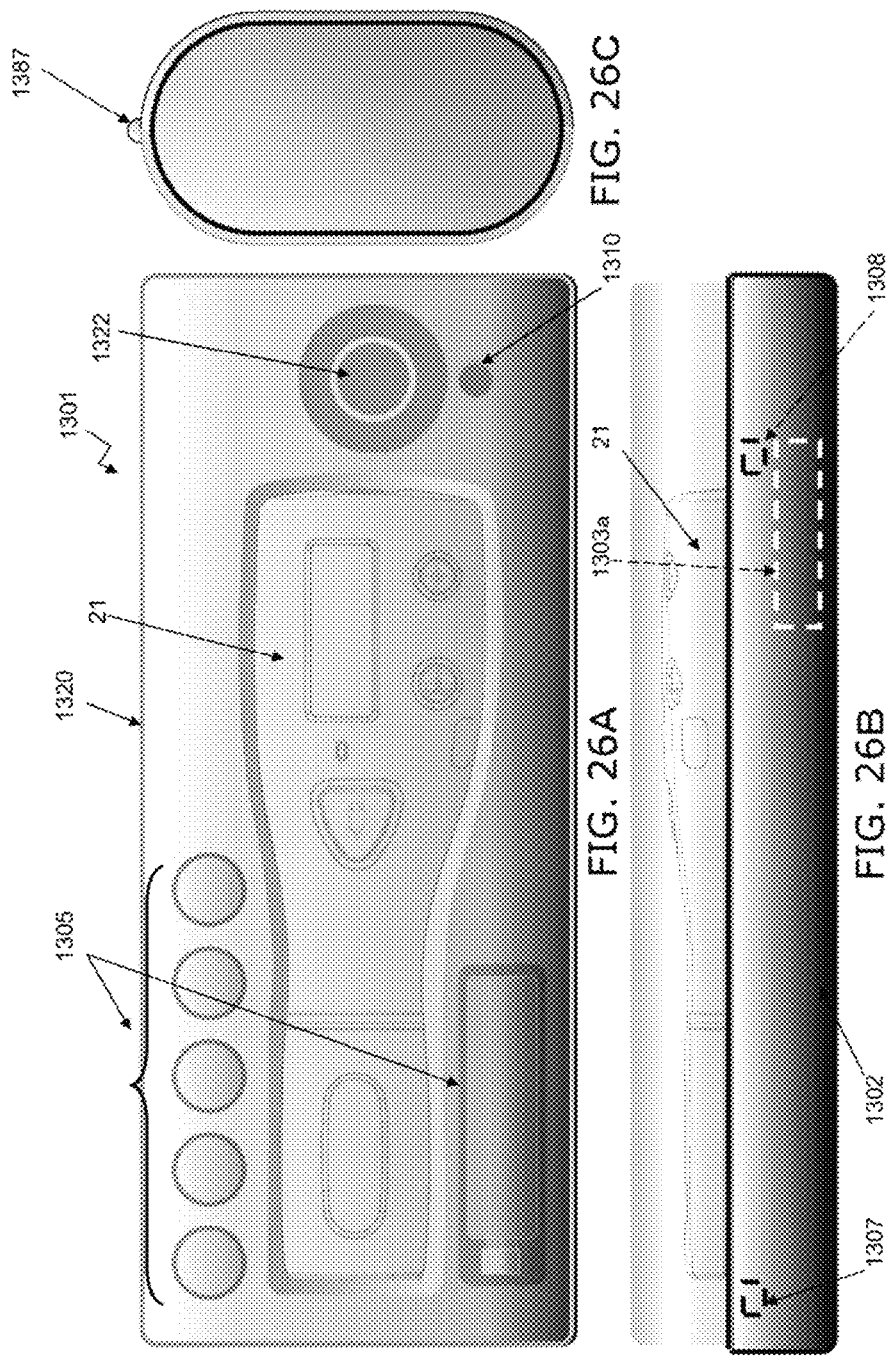

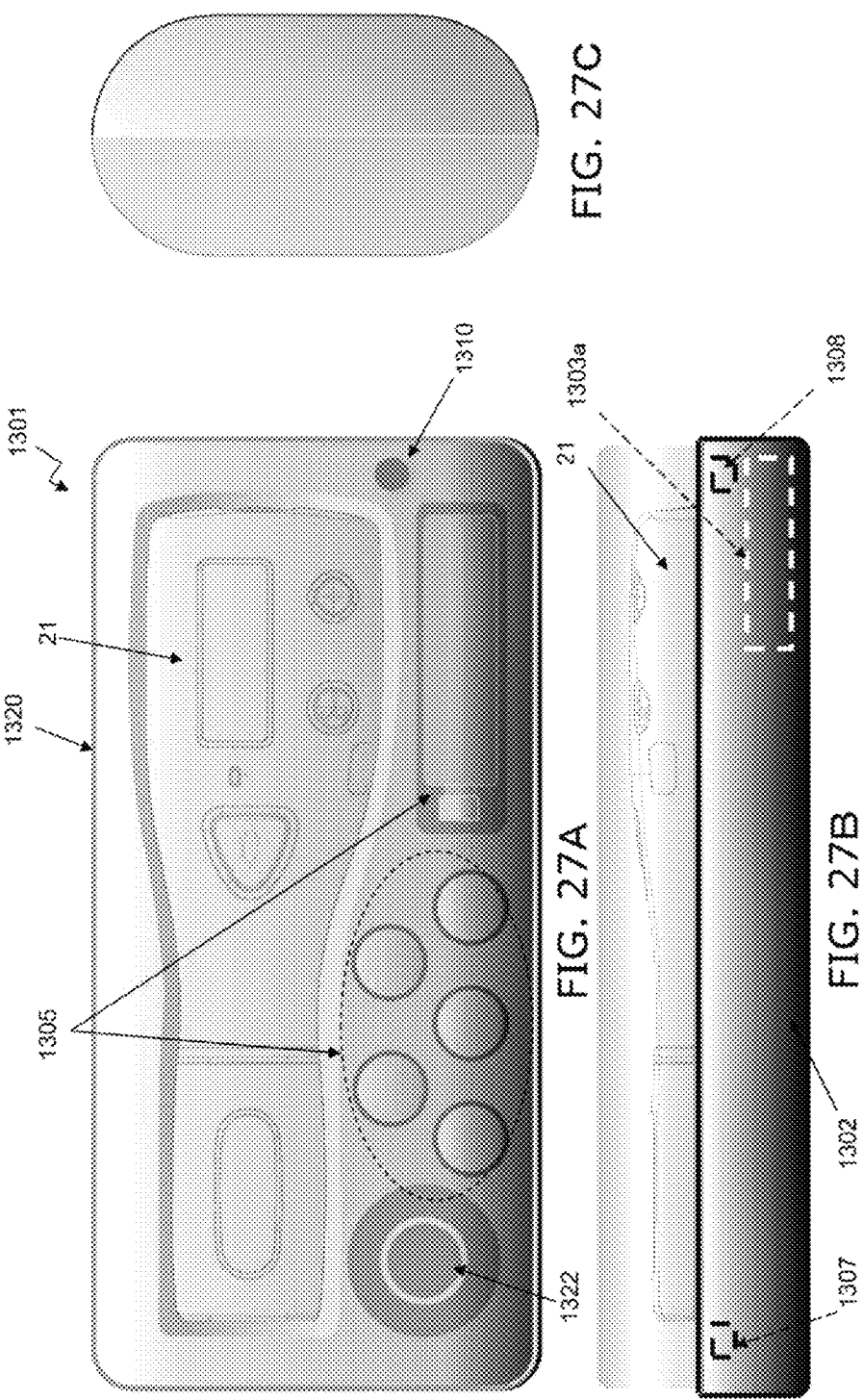

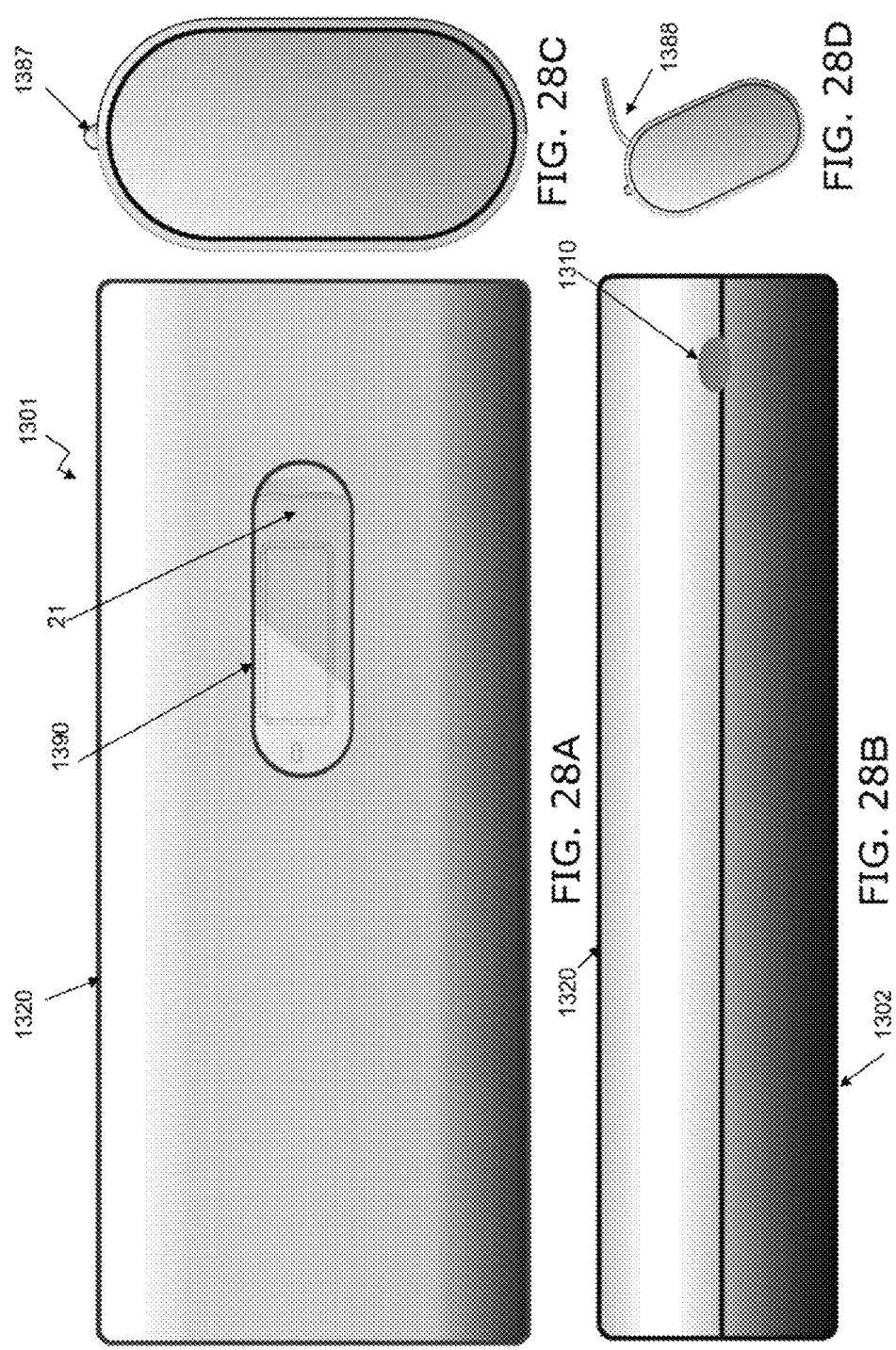

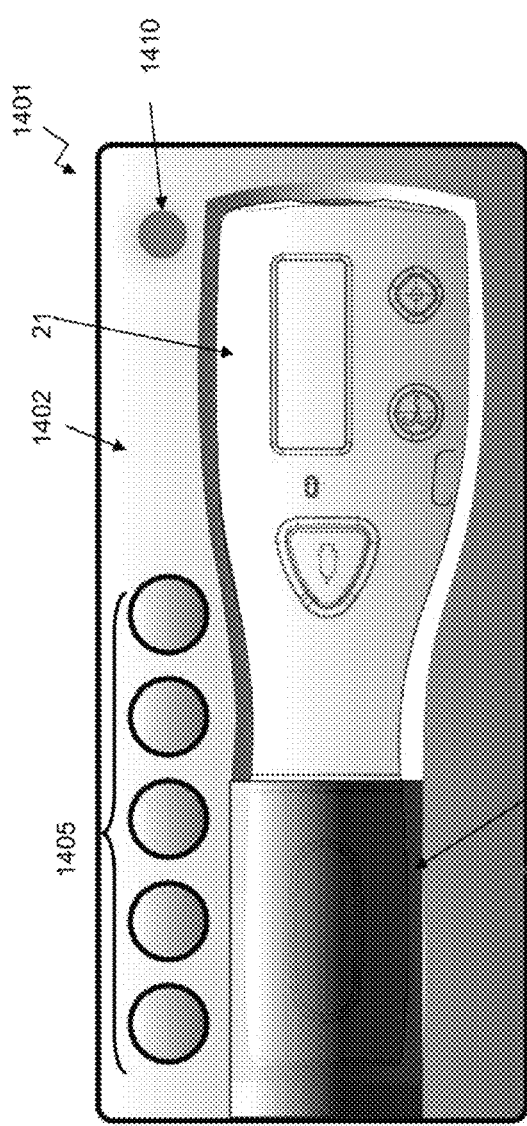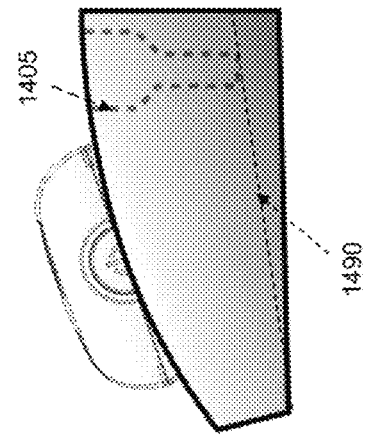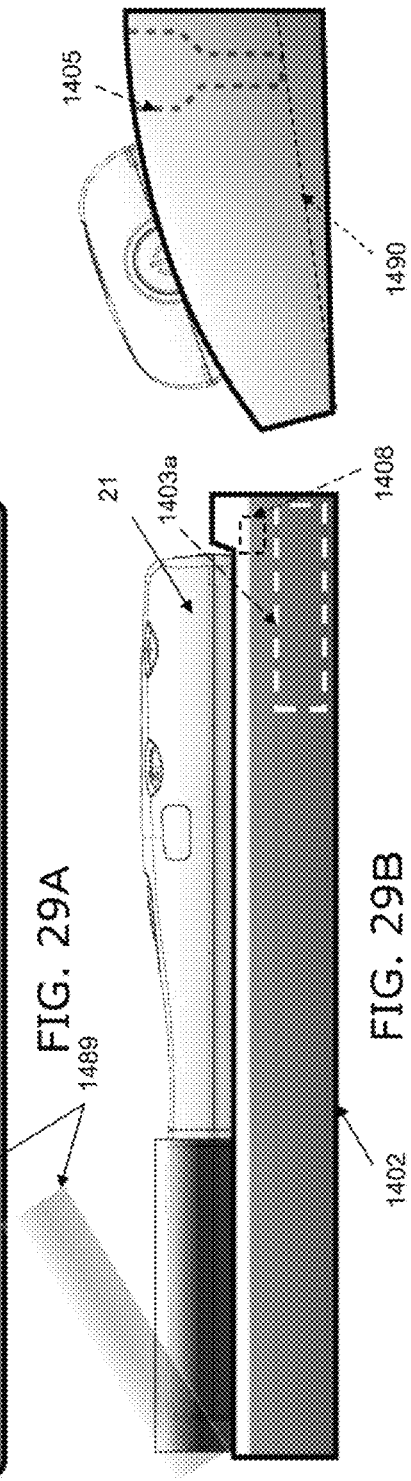

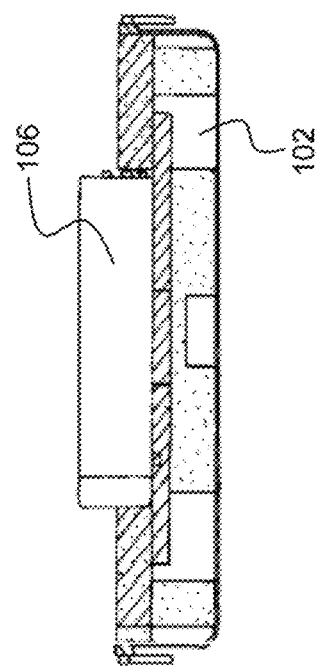
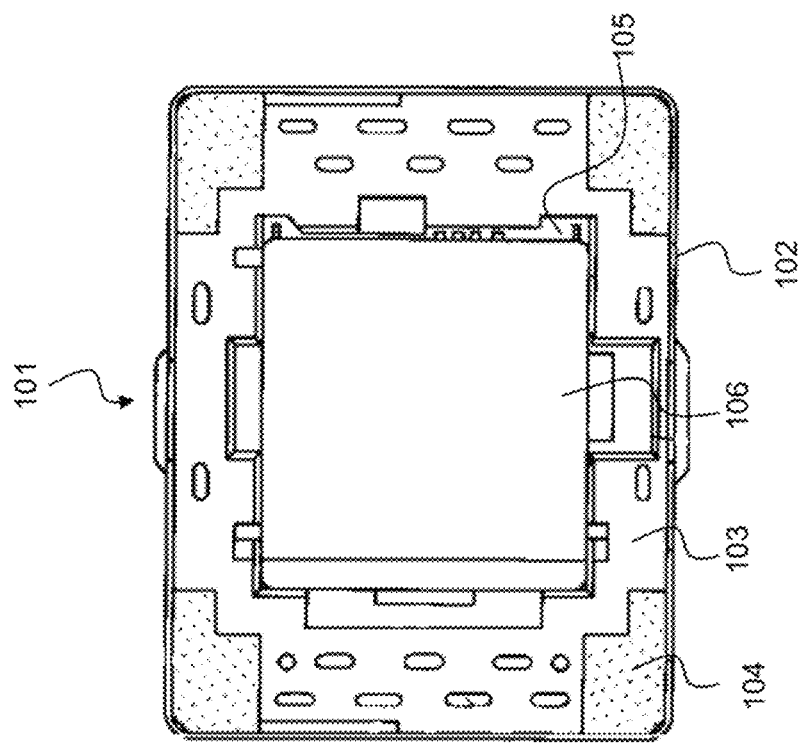
FIG. 30B
FIG. 30A

CARRYING CASE AND SYRINGE SYSTEM WITH SAME

TECHNICAL FIELD

The present invention relates to a carrying case for a pharmaceutical injection device equipped with a pharmaceutical syringe containing a pharmaceutical for administering the pharmaceutical to a living body, and relates to a syringe system with the same.

BACKGROUND ART

Well-known carrying cases have been designed to accommodate and carry a predetermined article, equipment attached to the article, and the like. Some of the well-known carrying cases that have been commercially viable so far include a type in which an accommodation section is entirely covered with a shock-absorbing material and a type in which such a shock-absorbing material is used as either a first shock-absorbing material or a second shock-absorbing material depending on situations.

FIGS. 30A and 30B illustrate an exemplary well-known carrying case. FIG. 30A illustrates a top view of a carrying case 101, whereas FIG. 30B illustrates a side view of the carrying case 101. As illustrated in the figures, the carrying case 101 includes a case unit 102, an article holding portion 105 for accommodating an article 106, and a lid (not illustrated in the figure). Further, the case unit 102 includes a first shock-absorbing material 103 and a second shock-absorbing material 104 in the inside thereof for protecting the article 106 from shocks (see e.g., Patent Literature 1).

The carrying case 101 can thus mitigate shocks to be applied to the article 106.

CITATION LIST

Patent Literature

Patent Literature 1: Specification of Japanese Patent No. 3010787

SUMMARY

Technical Problem

However, when an article accommodated in the aforementioned well-known carrying case 101 is an electronic device, an accurate instrument or the like requiring electrical power, a user is required to carry an electric charging device (electric charger) with him/her for charging the device or the instrument, in addition to the carrying case. Therefore, a user is required to make the space for accommodating an electric charging device. Furthermore, it may sometimes happen that a user may forget to bring the electric charging device with him/her.

Meanwhile, the carrying case 101 does not include enough space to accommodate the other equipment and thereby cannot accommodate spare pharmaceuticals for which temperature control is required. The carrying case 101 thereby lacks convenience.

It is an object of the present invention to provide a carrying case and a syringe system for allowing a user to use a pharmaceutical injection device easily and safely.

Solution to Problem

A carrying case according to a first aspect of the present invention is a carrying case for a pharmaceutical injection device for administering a pharmaceutical to a living body and includes a case unit and an electric charging device. The case unit is configured to accommodate the pharmaceutical injection device therein. The electric charging device is mounted in the case unit. The electric charging device includes an electric charging terminal electrically connectable to the pharmaceutical injection device. The electric charging device is configured to electrically charge the pharmaceutical injection device.

The following structure is adopted herein for the carrying case configured to accommodate the pharmaceutical injection device so that a user no longer needs to separately carry an electric charging device with him/her.

The carrying case includes the case unit, and the electric charging device is mounted and fixed to the case unit for electrically charge the pharmaceutical injection device. The electric charging device includes the electric charging terminal electrically connectable to the pharmaceutical injection device.

The pharmaceutical injection device may be, for instance, an electronic device that accommodates a syringe containing a pharmaceutical and automatically injects the pharmaceutical into a living body. The aforementioned case unit may be a case unit that outlines the carrying case and includes, for instance, a pair of a bottom case and a cover connected to each other by means of a hinge in an openable/closable manner. "Electrically connectable" refers to a state that power supply is available, and may be a state that conductive members are connected to each other or a non-contact state using electromotive force or the like (by means of a non-contact electric charging method). The electric charging device includes, for instance, a power supply circuit for electric charging, and may include a primary battery and/or an AC adaptor for supplying electric power to the power supply circuit, a jack for allowing an AC adaptor to be connected thereto, or the like.

Well-known carrying cases for accommodating electronic devices (including portable electronic devices) and the like enclose shock-absorbing materials and the like for absorbing shocks. However, users are required to separately carry the electric charging devices for supplying electric power to the electronic devices. Therefore, users are required to secure the spaces for accommodating the electric charging devices and may forget to bring the electric charging devices with them in some cases.

In view of the above, the carrying case of the present invention includes the electric charging device in the case unit.

The structure allows a user to bring the pharmaceutical injection device and the electric charging device required for electrically charging the pharmaceutical injection device while both of them are fixed to the carrying case. In other words, a user is allowed to bring an electric charging device and a pharmaceutical injection device in a single carrying case.

As a result, a user is no longer required to secure the space for accommodating an electric charging device in the carrying case and separately carry an electric charging device with him/her, and the like. It is thereby possible to prevent such a situation that electric charging is not available when a user is out because he/she forgets to bring an electric charging device with him/her.

A carrying case according to a second aspect of the present invention relates to the carrying case according to the first aspect of the present invention, in which the electric charging device includes a connector allowing an AC adaptor to be connected thereto.

The connector may be, for instance, a plug-in jack, a connector mounted on a circuit board included in the electric charging device, or the like.

It is thereby possible to connect an external AC adaptor to the electric charging device or to accommodate an AC adaptor electrically connected to the electric charging device in the carrying case.

As a result, the electric charging device is allowed to receive electric power from a commercial power source through an AC adaptor.

A carrying case according to a third aspect of the present invention relates to the carrying case according to one of the first and second aspects of the present invention. In the carrying case, the electric charging device includes an AC adaptor. The AC adaptor is electrically connected to the connector.

The electric charging device includes an AC adaptor.

Preferably, the AC adaptor has a plug portion protruded to the outside of the case unit. The plug portion may be configured to be protruded by means of a slide mechanism or the like.

It is thereby possible to preliminarily include an AC adaptor in the carrying case. Therefore, a user is no longer required to separately carry an AC adaptor with him/her.

As a result, it is possible to prevent a user from forgetting to bring an AC adaptor with him/her.

A carrying case according to a fourth aspect of the present invention relates to the carrying case according to one of the first to third aspects of the present invention. In the carrying case, the electric charging device includes a primary battery.

The electric charging device includes a primary battery for electrically charging the pharmaceutical injection device.

The primary battery herein refers to a battery that can supply electric power by itself.

It is thereby possible to supply electric power for charging to the pharmaceutical injection device from the primary battery without supplying electric power for charging thereto from the outside. Therefore, a user is allowed to execute electric charging of the pharmaceutical injection device even when he/she is in a place without a commercial power source or when he/she is moving. Further, the AC adaptor and the primary battery may be selectively used depending on situations.

As a result, it is possible to provide a user-friendly carrying case with the electric charging function using a generally prevalent primary battery.

A carrying case according to a fifth aspect of the present invention relates to the carrying case according to the first aspect or the fourth aspect of the present invention. In the carrying case, the electric charging device includes a rechargeable battery. The electric charging device is configured to electrically charge the rechargeable battery.

It is thereby possible to more reliably supply electric power to the pharmaceutical injection device.

A carrying case according to a sixth aspect of the present invention relates to the carrying case according to the first aspect of the present invention. In the carrying case, the electric charging device includes either a manual electric charging unit or a solar battery unit.

It is thereby possible to more reliably supply electric power to the pharmaceutical injection device.

A carrying case according to a seventh aspect of the present invention relates to the carrying case according to the fifth aspect of the present invention. In the carrying case, the electric charging device is configured to electrically charge either the pharmaceutical injection device or the rechargeable battery in a non-contact manner.

It is thereby possible to more easily supply electric power to the pharmaceutical injection device.

A carrying case according to an eighth aspect of the present invention relates to the carrying case according to one of the first to seventh aspects of the present invention. In the carrying case, the case unit includes a recess for accommodating the pharmaceutical injection device. The electric charging terminal of the electric charging device is protruded from the recess in a retractable manner.

The electric charging terminal is protruded from the recess for accommodating the pharmaceutical injection device in a retractable manner.

It is thereby possible to electrically connect a terminal receiver of the pharmaceutical injection device to the electric charging terminal while the pharmaceutical injection device is placed (accommodated) in the recess of the case unit. Therefore, the pharmaceutical injection device is allowed to be electrically charged while being accommodated in the case unit. The terminal receiver of the pharmaceutical injection device herein refers to a section allowing the electric charging terminal to be electrically connected thereto. The terminal receiver is electrically connected to a rechargeable battery (battery) provided in the pharmaceutical injection device.

As a result, it is possible to provide a carrying case that allows a pharmaceutical injection device to be accommodated therein and to be electrically charged easily.

A carrying case according to a ninth aspect of the present invention relates to the carrying case according to the eighth aspect of the present invention. In the carrying case, the electric charging device includes an elastic member attached to the electric charging terminal and configured to urge the electric charging terminal to be protruded from the top of the recess of the case unit.

Examples of the elastic member include a metal spring such as a coil spring, a resin spring such as urethane and rubber, or other members made of material with elasticity.

It is thereby possible to eliminate variation in sizes among the pharmaceutical injection device, the case unit and the electric charging device when the terminal receiver of the pharmaceutical injection device and the electric charging terminal of the electric charging device make contact with each other. Therefore, the electric charging terminal and the terminal receiver are allowed to reliably make contact with each other while the pharmaceutical injection device is accommodated in the recess of the case unit.

As a result, it is possible to prevent a failure of electric charging due to loose connection and avoid troubles such as shortage of electric power in use.

A carrying case according to a tenth aspect of the present invention relates to the carrying case according to the first aspect of the present invention. In the carrying case, the case unit includes an openable/closable pair of a cover and a bottom case. The electric charging device is configured to stop or start electric charging in conjunction with an opening or a closing action of the cover and the bottom case.

Electric charging is allowed to be stopped or started in conjunction with an opening action or a closing action of the case unit. Therefore, it is possible to automatically execute an electric charging operation without making a user aware of it.

A carrying case according to an eleventh aspect of the present invention relates to the carrying case according to the first aspect of the present invention. The carrying case further includes a display unit.

It is thereby possible to enhance convenience of the carrying case.

A carrying case according to a twelfth aspect of the present invention relates to the carrying case according to the eleventh aspect of the present invention. In the carrying case, the display unit is configured to execute a display operation using a liquid crystal, an organic EL or an LED.

A carrying case according to a thirteenth aspect of the present invention relates to the carrying case according to the eleventh aspect or the twelfth aspect of the present invention. In the carrying case, the display unit is configured to display an electric charging status, a data communication status, a conduction status or error content.

A carrying case according to a fourteenth aspect of the present invention relates to the carrying case according to the thirteenth aspect of the present invention. In the carrying case, the display unit is configured to display, as the electric charging status, a remainder frequency of pharmaceutical injections by the pharmaceutical injection device.

A carrying case according to a fifteenth aspect of the present invention relates to the carrying case according to the first aspect of the present invention. The carrying case further includes at least either of an audio unit and a vibration unit. At least either of the audio unit and vibration unit is configured to inform a user of predetermined information by means of an audio guide, an alert buzzer or a vibration.

The predetermined information herein refers to a current status of the carrying case such as an electric charging status, a communication status, a conduction status, warning, caution or the like (e.g., the remaining available number of times for injections by the pharmaceutical injection device based on the amount of injected pharmaceutical agent). The audio unit is configured to inform a user of the predetermined information by means of a buzzer, a sounder, a speaker or the like. The vibration unit is configured to cause a vibrator or the like to generate vibrations in the carrying case and thereby inform a user of the predetermined information.

It is thereby possible to inform a visually and/or auditory disabled user of information. Therefore, it is possible to enhance convenience and safety of the carrying case.

A carrying case according to a sixteenth aspect of the present invention relates to the carrying case according to the first aspect of the present invention. The carrying case further includes an input unit configured to receive an information input by a user.

The input unit herein may be built in the carrying case or an external input unit.

A carrying case according to a seventeenth aspect of the present invention relates to the carrying case according to the first aspect of the present invention. In the carrying case, the case unit further includes a lock mechanism. The lock mechanism is configured to secure the pharmaceutical injection device to the case unit such that the electric charging terminal of the electric charging device makes contact with a terminal receiver of the pharmaceutical injection device.

The lock mechanism herein secures the pharmaceutical injection device to the electric charging device.

For example, it is possible to use, as the lock mechanism, an engaging member configured to secure the electric charging device and the pharmaceutical injection device with each other by the electric charging device engaging with a part of the pharmaceutical injection device. When the electric charging terminal is protruded from the recess, the lock mechanism is preferably disposed such that the pharmaceutical injection device is secured to the recess.

It is thereby possible to reliably secure the pharmaceutical injection device to the electric charging device. When the electric charging terminal is protruded from the recess, the pharmaceutical injection device can be reliably in contact with and fixed to the electric charging device while being secured to the recess.

As a result, the pharmaceutical injection device can be prevented from being removed from the electric charging device due to vibrations or shocks. Therefore, the pharmaceutical injection device can be reliably electrically charged.

A carrying case according to an eighteenth aspect of the present invention relates to the carrying case according to the first aspect of the present invention. In the carrying case, the case unit includes an openable/closable pair of a cover and a bottom case. The cover includes a transparent window portion, a translucent window portion or a cutout window portion.

The carrying case is divided into a cover and a bottom case. The cover is provided with a window portion for allowing a user to check whether or not the pharmaceutical injection device is accommodated in the carrying case.

The cover and the bottom case are preferably connected to each other by means of, for instance, a hinge or the like. For example, a transparent plastic, glass or the like may be used for the window portion.

It is thereby possible for a user to visually check the inside of the carrying case through the window portion. Therefore, a user is allowed to easily check whether or not the pharmaceutical injection device is accommodated in the carrying case.

As a result, it is possible to prevent a user from forgetting to put the pharmaceutical injection device in the carrying case.

A carrying case according to a nineteenth aspect of the present invention relates to the carrying case according to the eighteenth aspect of the present invention. In the carrying case, the bottom case includes an engaging mechanism. The engaging mechanism is configured to engage with the cover when the cover is in a closed state.

Preferably, the engaging mechanism is, for instance, a slide knob including a slide mechanism or the like.

It is thereby possible to control opening and closing of the cover and the bottom case. Therefore, it is possible to prevent the carrying case from being accidentally opened.

As a result, a user can safely carry the carrying case with him/her.

A carrying case according to a twentieth aspect of the present invention relates to the carrying case according to the eighteenth aspect or the nineteenth aspect of the present invention. In the carrying case, the cover includes an equipment presser rib. The equipment presser rib is configured to hold equipment for the pharmaceutical injection device to be accommodated in the bottom case.

The cover is provided with the equipment presser rib for holding equipment necessary for the pharmaceutical injection device.

The equipment includes a needle to be used for the pharmaceutical injection device, a spare pharmaceutical syringe and the like. The bottom case is preferably provided with an equipment accommodation portion for accommodating the aforementioned equipment.

The equipment can be thereby held while the cover is closed. Therefore, the equipment can be prevented from being scattered in the carrying case.

As a result, it is possible to provide a carrying case that is more user-friendly than well-known carrying cases.

A carrying case according to a twenty-first aspect of the present invention relates to the carrying case according to one of the eighteenth to twentieth aspects of the present invention. In the carrying case, the cover includes a first shock-absorbing member in an inner side thereof for protecting the pharmaceutical injection device.

The shock-absorbing member includes a material for absorbing shocks, and may be made of rubber.

Even when the pharmaceutical injection device collides against the inside of the cover when the carrying case is in a closed state, shocks can be mitigated.

As a result, it is possible to provide the carrying case for protecting the pharmaceutical injection device from being damaged or broken.

A carrying case according to a twenty-second aspect of the present invention relates to the carrying case according to one of the first to twenty-first aspects of the present invention. In the carrying case, the electric charging device includes a second shock-absorbing member for protecting electronic components included in the electric charging device from shocks.

It is thereby possible to protect a primary battery, a power supply circuit or the like included in the electric charging device from shocks.

A carrying case according to a twenty-third aspect of the present invention is a carrying case configured to accommodate a pharmaceutical injection device for administering a pharmaceutical to a living body. The carrying case includes: a case unit accommodating the pharmaceutical injection device therein; and a temperature regulation unit configured to regulate a temperature within the case unit. The temperature regulation unit includes: a cooling execution section configured to execute a cooling operation; a cooling fan configured to supply a cool air into the case unit; and a cooling control section configured to control the cooling execution section.

The carrying case includes the temperature regulation unit and a cool air is supplied to the inside of the case unit by controlling and executing a cooling operation. Accordingly, a user is allowed to carry the pharmaceutical that requires a temperature control with him/her using the carrying case. Therefore, it is possible to enhance safety and convenience of the carrying case.

A carrying case according to a twenty-fourth aspect of the present invention relates to the carrying case according to the twenty-third aspect of the present invention. In the carrying case, the case unit further includes at least one temperature sensor. The cooling control section of the temperature regulation unit is configured to control the cooling execution section based on a value/values measured by the at least one temperature sensor.

For example, the cooling control section is configured to calculate a difference between the temperature data of the temperature sensor/sensors and a preliminarily set cooling setting temperature. The cooling control section then regulates the temperature inside the case unit by controlling a cooling level (rapid cooling, strong cooling, intermediate cooling, weak cooling and the like) in accordance with that temperature difference.

It is thereby possible to automatically regulate the temperature in the inside of the carrying case.

A carrying case according to a twenty-fifth aspect of the present invention relates to the carrying case according to the twenty-third aspect of the present invention. The carrying case further includes an electric charging device. The electric charging device is mounted in the case unit, includes an electric charging terminal electrically connectable to the pharmaceutical injection device, and is configured to electrically charge the pharmaceutical injection device. Further, the temperature regulation unit is configured to be operated by electric power supplied from the electric charging device.

It is thereby possible to operate the temperature regulation unit by electric power supplied by the electric charging device. Therefore, it is possible to stably regulate the temperature in the inside of the carrying case.

A carrying case according to a twenty-sixth aspect of the present invention relates to the carrying case according to the twenty-third aspect of the present invention. In the carrying case, the case unit includes an openable/closable pair of a cover and a bottom case. The temperature regulation unit is configured to stop or start a cooling operation in conjunction with an opening action or a closing action of the cover and the bottom case.

It is possible to stop or start the cooling operation in conjunction with the opening or closing action of the case unit. Therefore, it is possible to automatically control a cooling operation in the inside of the carrying case without making a user aware of it.

A carrying case according to a twenty-seventh aspect of the present invention relates to the carrying case according to the twenty-third aspect of the present invention. In the carrying case, the case unit is made of a material having either a thermal insulation property or a sealing property.

It is thereby possible to enhance a cooling effect in the inside of the carrying case.

A carrying case according to a twenty-eighth aspect of the present invention relates to the carrying case according to the twenty-third aspect of the present invention. In the carrying case, the case unit has a sealing member attached on an outer surface thereof.

It is thereby possible to enhance a cooling effect in the inside of the carrying case.

A carrying case according to a twenty-ninth aspect of the present invention relates to the carrying case according to the twenty-third aspect of the present invention. The carrying case further includes a display unit configured to display a temperature status in the inside of the case unit.

It is thereby possible for a user to see the temperature status in the inside of the carrying case.

A carrying case according to a thirtieth aspect of the present invention is a carrying case configured to accommodate a pharmaceutical injection device for administering a pharmaceutical to a living body. The carrying case includes a case unit accommodating the pharmaceutical injection device. The case unit includes at least one equipment accommodation portion configured to accommodate a single piece or plurality pieces of equipment required for the pharmaceutical injection device.

The carrying case includes the accommodation portion for accommodating the equipment. Accordingly, it is possible to enhance safety and convenience of the carrying case.

A carrying case according to a thirty-first aspect of the present invention relates to the carrying case according to the thirtieth aspect of the present invention. In the carrying case, the at least one equipment accommodation portion is configured to accommodate at least one of the following equipment: a needle for the pharmaceutical injection device; a pharmaceutical syringe, a sterilization member; a used needle; a protection cap for the needle; a puncture device for collecting blood; a needle for the puncture device; a blood glucose meter for measuring a blood glucose level; a sensor to be used for the blood glucose meter; and a sensor bottle for accommodating the sensor.

A carrying case according to a thirty-second aspect of the present invention relates to the carrying case according to the thirtieth aspect of the present invention. In the carrying case, the case unit further includes an equipment holding portion configured to hold a protection cap for a needle thereon.

The equipment holding portion for holding the protection cap thereon is a portion for temporarily holding thereon the protection cap that has been removed from an unused needle for the pharmaceutical injection device while the pharmaceutical injection device with the unused needle attached thereon is in use, for instance. Then, the protection cap is attached to the used needle and then is discarded.

It is thereby possible for a user to more safely discard the needle after use.

A carrying case according to a thirty-third aspect of the present invention relates to the carrying case according to the thirtieth aspect of the present invention. In the carrying case, the case unit further includes a mixture portion configured to be inserted into an end of a pharmaceutical syringe for mixing the pharmaceutical within the pharmaceutical syringe.

It is thereby possible to mix the pharmaceuticals in the inside of the pharmaceutical syringe by inserting the mixture portion into the end of the pharmaceutical syringe. Accordingly, it is possible for a user to use the pharmaceutical syringe safely and easily.

A carrying case according to a thirty-fourth aspect of the present invention relates to the carrying case according to one of the first, twenty-third and thirtieth aspects of the present invention. In the carrying case, the case unit includes an inner case, and further includes a third shock-absorbing member between the case unit and the inner case.

The inner case herein refers to a component for appropriately positioning the pharmaceutical injection device within the case unit and for preventing collision between the case unit and the pharmaceutical injection device.

It is thereby possible to mitigate shocks applied to the inner case when the carrying case collides with something or falls to the ground or the like. Therefore, it is possible to protect, from the shocks, the components accommodated in the inner case such as a pharmaceutical injection device, equipment, and an electric charging device coupled to the inner case.

As a result, it is possible for a user to carry, with him/her, an accurate instrument/instruments such as an electric charging device or a pharmaceutical injection device, a glass product/products such as a pharmaceutical syringe, and/or the like, without damaging or breaking these components.

A carrying case according to a thirty-fifth aspect of the present invention relates to the carrying case according to one of the first, twenty-third and thirtieth aspects of the present invention. In the carrying case, the case unit is antibacterial.

It is thereby possible to prevent substances (e.g., blood) from being attached to the surface of the carrying case. Therefore, the carrying case achieves sanitation and also enhances safety.

A syringe system according to a thirty-sixth aspect of the present invention includes the carrying case according to one of the first, twenty-third and thirtieth aspects of the present invention and a pharmaceutical injection device configured to be accommodated in the carrying case.

It is thereby possible to provide a syringe system that allows a user to easily and reliably carry an electric charging device with him/her.

Advantageous Effects

According to the carrying case and the syringe system of the present invention, easy and safe usage of the pharmaceutical injection device can be assured.

BRIEF DESCRIPTION OF DRAWINGS

FIG. 3A is a cross-sectional view of the inside of the bottom case, and FIG. 3B is an enlarged cross-sectional view of a major part of the bottom case;

FIG. 16A to FIG. 16C are diagrams illustrating a series of actions of a two-pharmaceutical mixing portion of the carrying case illustrated in FIG. 14;

FIG. 18 illustrates patterns of a display unit for the carrying case according to the fourth exemplary embodiment of the present invention and for a carrying case according to a fifth exemplary embodiment of the present invention;

FIG. 20A to FIG. 20C are diagrams illustrating one configuration example of the carrying case of the present invention;

FIG. 21A to FIG. 21C are diagrams illustrating another configuration example of the carrying case of the present invention;

FIG. 22A to FIG. 22C are diagrams illustrating yet another configuration example of the carrying case of the present invention;

FIG. 23A to FIG. 23C are diagrams illustrating yet another configuration example of the carrying case of the present invention;

FIG. 24A to FIG. 24C are diagrams illustrating yet another configuration example of the carrying case of the present invention;

FIG. 25A to FIG. 25C are diagrams illustrating yet another configuration example of the carrying case of the present invention;

FIG. 26A to FIG. 26C are diagrams illustrating yet another configuration example of the carrying case of the present invention;

FIG. 27A to FIG. 27C are diagrams illustrating yet another configuration example of the carrying case of the present invention;

FIG. 28A to FIG. 28D are diagrams illustrating yet another configuration example of the carrying case of the present invention;

FIG. 29A to FIG. 29C are diagrams illustrating yet another configuration example of the carrying case of the present invention; and FIGS. 30A and 30B are a cross-sectional side view and a cross-sectional top view of a well-known carrying case, respectively.

DESCRIPTION OF EMBODIMENTS

1 First Exemplary Embodiment

FIGS. 1 to 4 illustrate a syringe system 50 including a carrying case 1 and a pharmaceutical injection device 21 according to a first exemplary embodiment of the present invention.

<1.1 Carrying Case 1>

Figure 1:
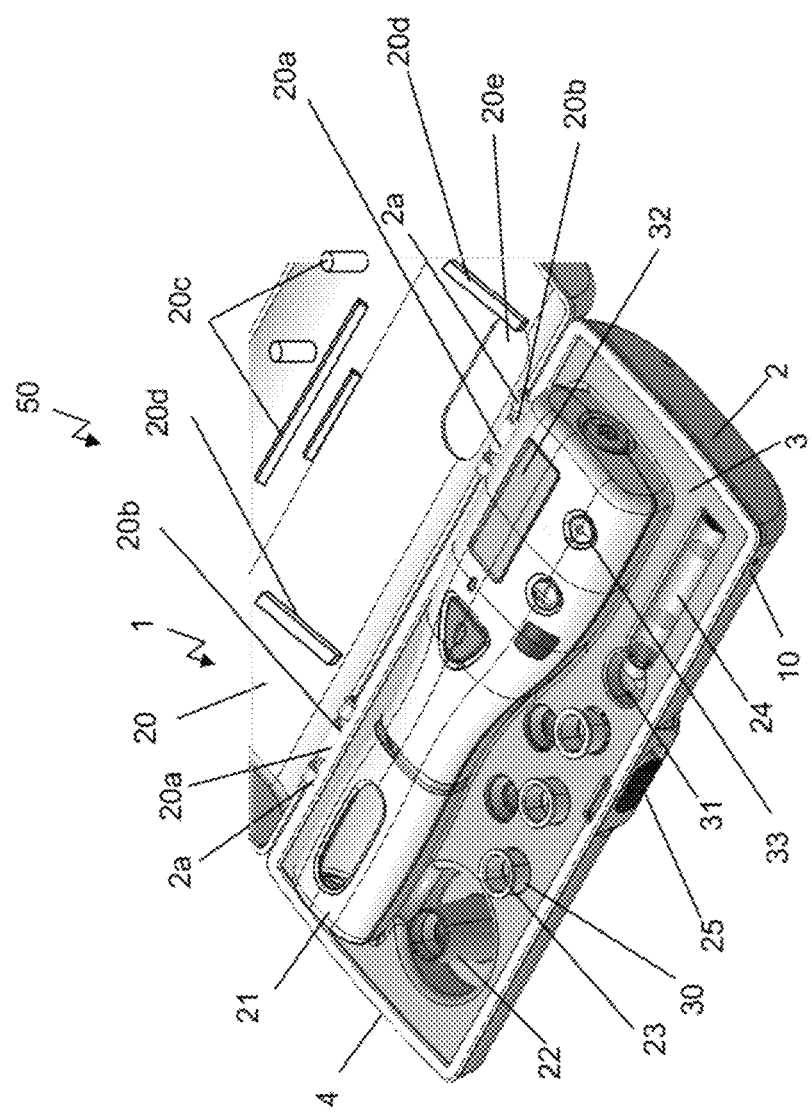
FIG. 1 is a perspective view of an opened state of a carrying case for a syringe system according to a first exemplary embodiment of the present invention.

As illustrated in FIG. 1, the carrying case 1 mainly includes a bottom case 2 (exemplifying a case unit), a bottom inner case 3 (exemplifying an inner case), a cover 20 (also exemplifying a case unit) and an electric charging device 3a (FIG. 3). It should be noted that FIG. 1 partially omits illustration of the configuration of the cover 20 but the omitted part has an outline similar to that of the bottom case 2.

<1.1.1 Cover 20>

The cover 20 forms a framework of the carrying case 1 with the bottom case 2. As illustrated in FIG. 1, the cover 20 includes a support shaft holding portion (or portions) 20a, a support shaft (or shafts) 20b, an equipment presser rib (or ribs) 20c, a shock-absorbing material (or materials) 20d (exemplifying a first shock-absorbing material) for protecting the pharmaceutical injection device 21, and a window portion 20e.

The support shaft holding portion (or portions) 20a is disposed in a coupling part of the cover 20 to the bottom case 2 and includes an aperture (or apertures) for press-fit insertion of the support shaft 20b in the inside thereof.

The support shaft (or shafts) 20b is held in the aperture (or apertures) of the support shaft holding portion (or portions) 20a while being inserted into a support shaft insertion portion (or portions) 2a of the bottom case 2. The structure allows the cover 20 and the bottom case 2 to be opened and closed.

The support shaft holding portion (or portions) 20a and the support shaft (or shafts) 20b form a hinge (or hinges).

The equipment presser rib (or ribs) 20c is disposed on the inner side of the cover 20. The equipment presser rib (or ribs) 20c is configured to press and hold the respective equipment pieces of the pharmaceutical injection device 21 while the carrying case 1 is in a closed state. The structure prevents the equipment from being scattered within the carrying case 1.

It should be noted that examples of the equipment pieces include an unused needle (or needles) 23, a pharmaceutical syringe or a syringe containing a spare pharmaceutical (or pharmaceuticals), which is hereinafter referred to as "a pharmaceutical syringe", a used needle (or needles), a protection cap (or caps) for a needle (or needles), a blood glucose meter for measuring a blood glucose level, a sensor (or sensors) to be used for the blood glucose meter, a sensor bottle for accommodating a sensor (or sensors), a sterilization member (or members), and other devices and parts such as a puncture device for collecting blood and a needle (or needles) for the puncture device.

The shock-absorbing material (or materials) 20d is disposed on the inner side of the cover 20. The shock-absorbing material (or materials) 20d is configured to press and hold the pharmaceutical injection device 21 while the carrying case 1 is in a closed state. The structure can mitigate shocks to be applied to the carrying case 1 due to falling, vibration, collision or the like. The pharmaceutical injection device 21 can be thereby protected from such shocks.

The window portion 20e is arranged in such a position that a user can see a pharmaceutical injection device 21 accommodated in the carrying case 1 through the window portion 20e from the outside while the carrying case 1 is in a closed state. The window portion 20e is made of transparent or translucent plastic or glass, or is alternatively formed as a cutout. Accordingly, a user is allowed to visually check whether or not the pharmaceutical injection device 21 is accommodated in the carrying case 1 without opening the carrying case 1.

<1.1.2 Bottom Case 2>

Figure 2:
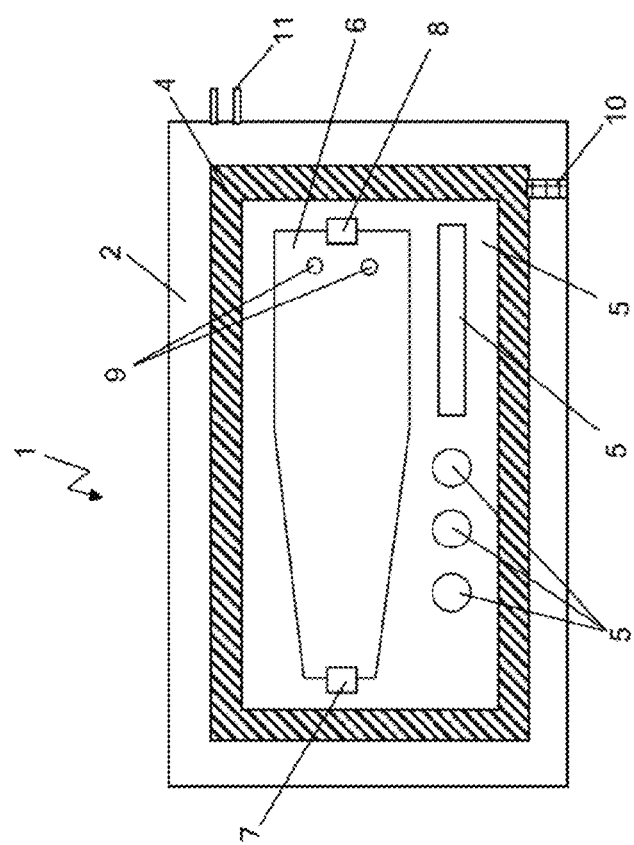
FIG. 2 is a schematic top view of a bottom case of the carrying case illustrated in FIG. 1.

As described above, the bottom case 2 forms a framework of the carrying case 1 with the cover 20. As illustrated in FIGS. 1 and 2, the bottom case 2 includes a shock-absorbing material 4, other shock-absorbing material (or materials) 14 (see FIG. 3A), the support shaft insertion portion (or portions) 2a and a slide knob 25 (exemplifying an engaging mechanism). Further, the bottom case 2 has a flat bottom surface. The carrying case 1 is thereby stably placed on a table or the like.

As illustrated in FIG. 3A, the shock-absorbing material 4 is disposed between the bottom case 2 and the bottom inner case 3 while being disposed along the inner outline of the bottom case 2. The structure can mitigate shocks applied to the bottom case 2 from the outside. In other words, the structure can protect the bottom inner case 3 and the articles accommodated in the bottom inner case 3 from the external shocks.

The shock-absorbing material (or materials) 14 is interposed between the bottom case 2 and a collar (collars) 15 that surrounds a screw (or screws) 16. The screw (or screws) 16 securely couples the bottom case 2 and the bottom inner case 3. It should be noted that the screw (or screws) 16 is preferably made of elastic resin. Meanwhile, the collar (or collars) 15 is a tubular member (or members) disposed on the outer periphery of the screw (or screws) 16. Similarly to the shock-absorbing material 4, the structure can protect the bottom inner case 3 and the articles accommodated in the inside of the bottom inner case 3.

The support shaft insertion portion (or portions) 2a is disposed in the coupling part between the bottom case 2 and the cover 20. As described above, the support shaft (or shafts) 20b is inserted into the support shaft insertion portion (or portions) 2a, so the support shaft insertion portion (or portions) 2a functions as a bearing (or bearings).

The slide knob 25 is disposed on a side surface of the carrying case 1. The slide knob 25 is configured to be engaged with an engaged portion (not illustrated in the figures) of the cover 20 by sliding a slide portion thereof for closing the carrying case 1. The bottom case 2 and the cover 20 are thereby locked to each other. Accordingly, the carrying case 1 can be prevented from being unnecessarily opened.

<1.1.3 Bottom Inner Case 3>

The bottom inner case 3 outlines accommodating positions for articles. As illustrated in FIG. 2, the bottom inner case 3 is disposed in the inner side of the bottom case 2 with the shock-absorbing material 4 therebetween. The bottom inner case 3 is securely coupled to the bottom case 2 by means of the screw (or screws) 16. Further, the bottom inner case 3 includes a main body accommodation portion 6 (recess) and an equipment accommodation portions 5.

The main body accommodation portion 6 is a recess for accommodating the pharmaceutical injection device 21 and has a shape for allowing a roughly bottom half of the pharmaceutical injection device 21 to be fitted therein.

As illustrated in FIG. 1, the equipment accommodation portions 5 includes a needle accommodation portion (or portions) 30, a pharmaceutical accommodation portion 31 and a needle protection cap holding portion 22 (exemplifying an equipment holding portion). The needle accommodation portion (or portions) 30 is a portion (or portions) for accommodating the unused needle (or needles) 23 to be attached to the pharmaceutical injection device 21 for injecting medical solution. The needle accommodation portion 30 is recessed so as to match with the shape of the unused needle 23. A protection cap (or caps) is attached to the unused needle (or needles) 23. The pharmaceutical accommodation portion 31 is a portion for accommodating a spare pharmaceutical syringe 24 containing medical solution. The pharmaceutical accommodation portion 31 is recessed so as to match with the shape of the spare pharmaceutical syringe 24. The protection cap holding portion 22 is a recess for allowing a protection cap (or caps) of the unused needle (or needles) to be temporarily held therein, for instance, when the pharmaceutical injection device 21 attached with the unused needle that has been removed from the protection cap is in use.

<1.1.4 Electric Charging Device 3a>

As illustrated in FIGS. 3A and 3B, the electric charging device 3a is configured to electrically charge the pharmaceutical injection device 21. The electric charging device 3a is embedded between the bottom inner case 3 and the bottom case 2. The electric charging device 3a includes an electric charging unit 17, a power supply printed circuit board 13, an LED 10 (exemplifying a light source unit), lock arms 7 and 8 (exemplifying a lock mechanism), an AC adaptor 12 and a shock-absorbing material (or materials) 19 (exemplifying a second shock-absorbing material or materials).

The electric charging unit 17 is configured to be electrically connected to a terminal receiver 39 of the pharmaceutical injection device 21 when the pharmaceutical injection device 21 is electrically charged. The electric charging unit 17 includes an electric charging terminal 9 and an electric charging terminal spring 9a (exemplifying an elastic member).

The electric charging terminal 9 is electrically connected to the terminal receiver 39 that is a connector for electrically charging the pharmaceutical injection device 21. The electric charging terminal 9 is disposed such that one of the ends thereof penetrates the bottom inner case 3 and protrudes from the surface of the main body accommodation portion 6. In other words, the electric charging terminal 9 is formed such that, when the pharmaceutical injection device 21 is accommodated in the main body accommodation portion 6, the terminal receiver 39 of the pharmaceutical injection device 21 make contact with the protruded end of the electric charging terminal 9. Further, the electric charging terminal 9 is electrically connected to the power supply printed circuit board 13.

The electric charging terminal spring 9a urges the electric charging terminal 9 in a direction for making the electric charging terminal 9 protrude into the main body accommodation portion 6. The electric charging terminal spring 9a is coupled to the other of the ends (opposite to the aforementioned protruded end) of the electric charging terminal 9. When the pharmaceutical injection device 21 is accommodated in the main body accommodation portion 6, the electric charging terminal 9 is pressed against the urging force of the electric charging terminal spring 9a until the electric charging terminal 9 is not protruded into the main body accommodation portion 6 while making contact with the terminal receiver 39 of the pharmaceutical injection device 21. The terminal receiver 39 of the pharmaceutical injection device 21 thereby reliably makes contact with the electric charging terminal 9, and failure of electric charging can be thereby avoided.

Figure 4:
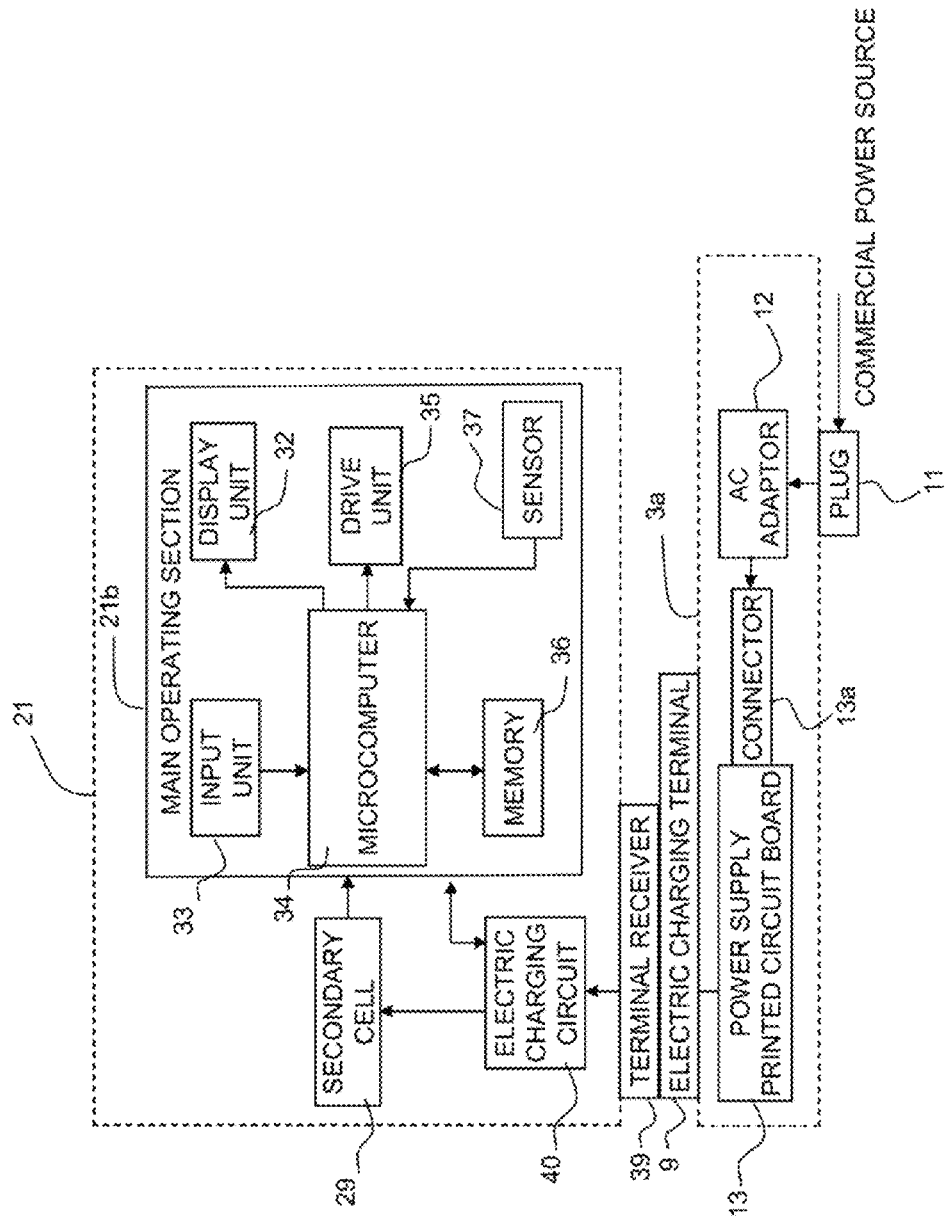
FIG. 4 is a block diagram of the syringe system illustrated in FIG. 1.

The power supply printed circuit board 13 is configured to regulate electric power supplied from the AC adaptor 12 and supply the electric power to the electric charging terminal 9, the LED 10 and the like. The power supply printed circuit board 13 is fixed between the bottom case 2 and the bottom inner case 3. In the present exemplary embodiment, the power supply printed circuit board 13 is fixed therein by means of a screw (screws) 18 as illustrated in FIG. 3 (b). Further, the power supply printed circuit board 13 is electrically connected to the AC adaptor 12, the electric charging terminal 9 and the LED 10. Yet further, the power supply printed circuit board 13 includes a connector 13a to be connected to the AC adaptor 12 as illustrated in FIG. 4. It should be noted that the connector 13a and the AC adaptor 12 may be detachable.

The lock arms 7 and 8 are configured to fix the pharmaceutical injection device 21 to the electric charging device 3a when the pharmaceutical injection device 21 is placed in the carrying case 1.

The AC adaptor 12 is configured to receive alternate current (AC) power from a commercial power source (AC power source, 100 V of AC) and convert AC power into direct current (DC) power. The adaptor 12 includes a plug 11. The plug 11 is used for connecting the AC adaptor 12 to an outlet. The plug 11 is disposed so as to protrude out of the bottom case 2. Specifically, the plug 11 may be fixedly disposed so as to protrude out of the bottom case 2. Alternatively, the plug 11 may be a slide type structure or a rotary type structure configured to be accommodated in the inside of the bottom case 2.

Further, a clearance 2b is provided between the AC adaptor 12 and the bottom case 2. It is possible to avoid the AC adaptor 12 and the bottom case 2 from making contact with each other and receiving load even when the bottom inner case 3 is displaced with respect to the bottom case 2 by the shocks due to falling, collision or the like.

The LED 10 is configured to indicate to a user whether or not the electric charging device 3a is chargeable. As illustrated in FIG. 1, the LED 10 is fitted in the bottom case 2. The LED 10 is electrically connected to the power supply printed circuit board 13. The LED 10 emits light when the electric charging device 3a is in a chargeable state, in other words, when the plug 11 is connected to an outlet and no malfunction (trouble) has occurred in the power supply printed circuit board 13 and the like in the present exemplary embodiment. It should be noted that the LED 10 may be disposed in the inside of the bottom case 2. In this case, any structures may be used as long as the light emitted by the LED 10 is brought to the outside of the bottom case 2 using a light guide plate or the like. Simply put, any structures may be used as long as a user is allowed to visually check the light of the LED 10 from the outside of the carrying case 1.

As illustrated in FIG. 3A, the lock arms 7 and 8 detachably fix the pharmaceutical injection device 21 to the main body accommodation portion 6 so that the terminal receiver 39 securely makes contact with the electric charging terminal 9. As illustrated in FIGS. 2 and 3A, the lock arms 7 and 8 are disposed on the side parts of the main body accommodation portion 6 of the bottom inner case 3. The lock arms 7 and 8 are respectively fixed so as to pivot about their fixed positions on the bottom inner case 3. Additionally, the lock arms 7 and 8 are respectively configured to be engaged with dents of the pharmaceutical injection device 21 by means of springs. The pharmaceutical injection device 21 can be thereby stably held within the carrying case 1.

The shock-absorbing material (or materials) 19 is disposed in the surrounding of the power supply printed circuit board 13 and the AC adaptor 12 for absorbing the shocks applied to the carrying case 1 due to falling, collision or the like. It is thereby possible to protect electronic components including the power supply printed circuit board 13, the AC adaptor 12 and the like.

<1.2 Pharmaceutical Injection Device 21>

The pharmaceutical injection device 21 is a device for administering a pharmaceutical to a living body from a pharmaceutical syringe. As illustrated in FIG. 4, the pharmaceutical injection device 21 mainly includes a main operating section 21b, a rechargeable battery 29 and an electric charging circuit 40.

The electric charging circuit 40 is configured to regulate electric power received through the electric charging device 3a of the carrying case 1 for supplying the electric power to the rechargeable battery 29. The electric charging circuit 40 is electrically connected to the terminal receiver 39. The electric charging circuit 40 is also controlled by a microcomputer 34.

The rechargeable battery 29 is a battery configured to be electrically charged for allowing the pharmaceutical injection device 21 to operate. The rechargeable battery 29 is electrically connected to the electric charging circuit 40.

The main operating section 21b includes a display unit 32, an input unit 33, the microcomputer 34, a drive unit 35, a memory 36 and a sensor 37.

The display unit 32 is a liquid crystal display or the like configured to display a variety of necessary information and messages regarding an operation of air vent in the pharmaceutical syringe, which will be describe later, the remaining battery level of the rechargeable battery 29 and the like.

The input unit 33 includes a button for switching power on/off of the pharmaceutical injection device 21, a button for air vent in the pharmaceutical syringe, a button for accepting procession to the next step when a necessary operation is done (e.g., when an air vent operation is done or when various display contents are acknowledged) and the like.

The microcomputer 34 is configured to control an entire operation of the pharmaceutical injection device 21.

The drive unit 35 is configured to displace a piston to push a pharmaceutical out of the syringe and inject the pharmaceutical into a living body through a syringe needle.

The memory 36 stores a variety of data to be used in the microcomputer 34.

The sensor 37 detects whether or not the AC adaptor 12 is connected to a power source.

Further, the carrying case 1 accommodates an unused needle (or needles) 23 and a spare pharmaceutical syringe 24 as equipment pieces of the pharmaceutical injection device 21.

<1.3 Features of First Exemplary Embodiment>

As illustrated in FIGS. 1 to 4, the carrying case 1 of the present exemplary embodiment is a carrying case for the pharmaceutical injection device 21 configured to administer a pharmaceutical to a living body, and includes a pair of the cover 20 and the bottom case 2 (exemplifying a case unit), the bottom inner case 3 and the electric charging device 3a. The case unit is allowed to be opened and closed. The bottom inner case 3 is fixed to the inside of the case unit and allows the pharmaceutical injection device 21 to be accommodated therein. The electric charging device 3a is fixed to the bottom inner case 3, includes the electric charging terminal 9 electrically connectable to the pharmaceutical injection device 21, and electrically charges the pharmaceutical injection device 21.

The structure allows a user to carry both the pharmaceutical injection device 21 and the electric charging device 3a with him/her while the two devices are fixed to the carrying case 1. In other words, a user can carry both the electric charging device 3a and the pharmaceutical injection device 21 in a single carrying case 1.

As a result, a user no longer needs to secure a space for accommodating the electric charging device within a carrying case 1 or separately carry an electric charging device 3a with him/her. Therefore, it is possible to prevent a situation that a user forgets to bring an electric charging device 3a with him/her and thereby cannot charge the pharmaceutical injection device when being out.

<1.4 Modifications of First Exemplary Embodiment>

(A)

In the aforementioned first exemplary embodiment, an example in which the AC adaptor 12 is disposed within the carrying case 1 has been given. However, the present exemplary embodiment is not limited to this.

Figure 5:
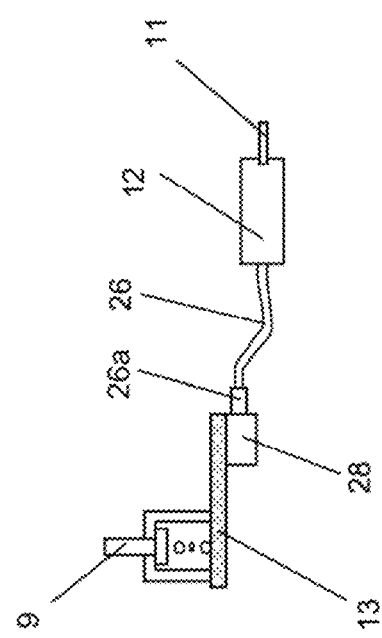
FIG. 5 is a side view of a major part of a carrying case according to a modification of the first exemplary embodiment.
Figure 6:
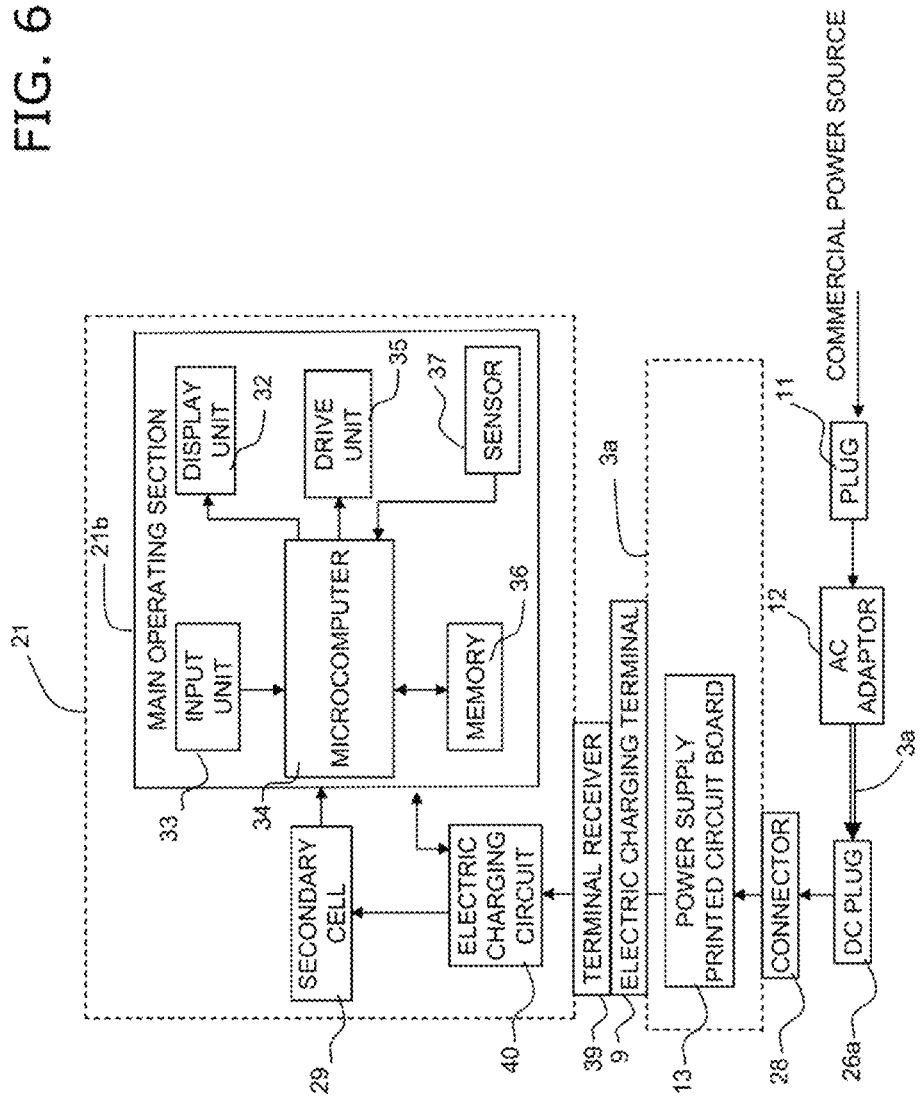
FIG. 6 is a block diagram of a syringe system including the carrying case illustrated in FIG. 5.

As illustrated in FIGS. 5 and 6, for instance, the AC adaptor 12 may be an external attachment component. Simply put, the carrying case 1 includes the AC adaptor 12 as an attachable/detachable component. Specifically, the carrying case 1 includes a jack (exemplifying a connector) 28. Further, the AC adaptor 12 includes a cord 26, a DC plug 26a and a plug 11. The DC plug 26a of the AC adaptor 12 is detachably connected to the jack 28.

The structure allows the pharmaceutical injection device 21 to be electrically charged by connecting the AC adaptor 12 to the jack 28 only when charging is necessary for the pharmaceutical injection device 21. Therefore, a user can carry the AC adaptor 12 with him/her depending on his/her needs.

As a result, a user is allowed to carry the carrying case 1 without AC adaptor 12 with him/her. In other words, it is possible to make the carrying case 1 more compact.

(B)

In the aforementioned first exemplary embodiment, an example in which the electric charging device 3a of the carrying case 1 includes an AC adaptor 12 and a commercial power source is used as a power supply source has been given. However, the present exemplary embodiment is not limited to this.

Figure 7:
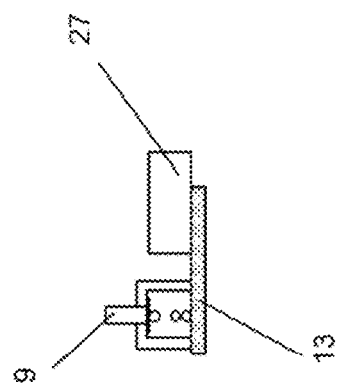
FIG. 7 is a side view of a major part of a carrying case according to another modification of the first exemplary embodiment.
Figure 8:
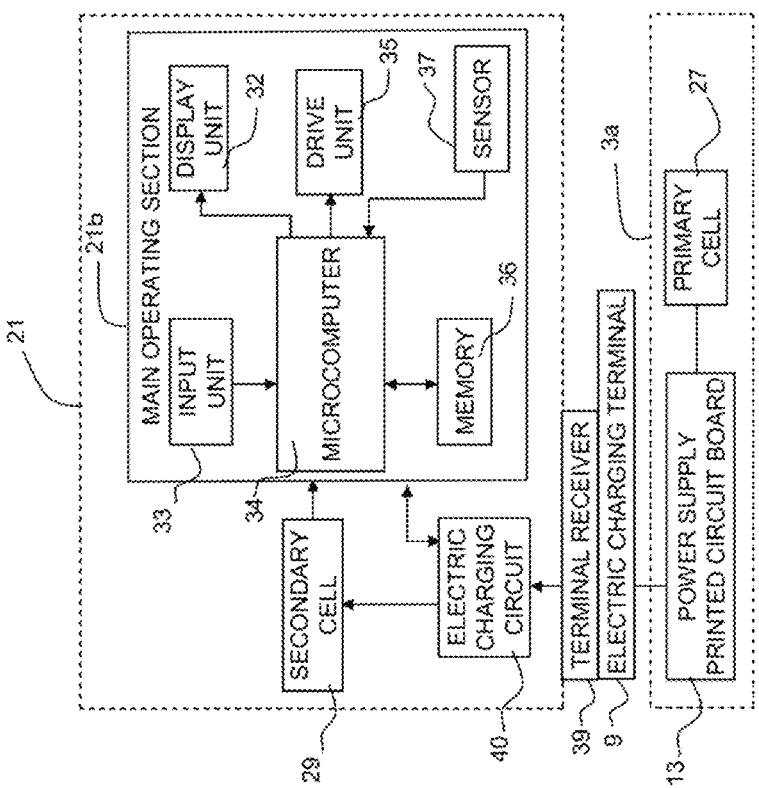
FIG. 8 is a block diagram of a syringe system including the carrying case illustrated in FIG. 7.

As illustrated in FIGS. 7 and 8, for instance, the electric charging device 3a of the carrying case 1 may include a primary battery 27 without having an AC adaptor. In this case, the carrying case 1 may include a plurality of primary batteries 27. Further, the primary battery 27 may be an alkaline cell, a manganese cell or the like. Yet further, the primary battery 27 is preferably replaceable.

With the structure, it is possible to supply a DC power from the primary battery 27 to the power supply printed circuit board 13 and electrically charge the rechargeable battery 29 of the pharmaceutical injection device 21 through the electric charging terminal 9.

In other words, the carrying case 1 is not equipped with an AC adaptor therein and can be thereby lightweight. Further, a user does no longer need to carry an AC adaptor with him/her as an external attachment component. Therefore, it is possible to provide a highly portable carrying case.

(C)

Figure 9:
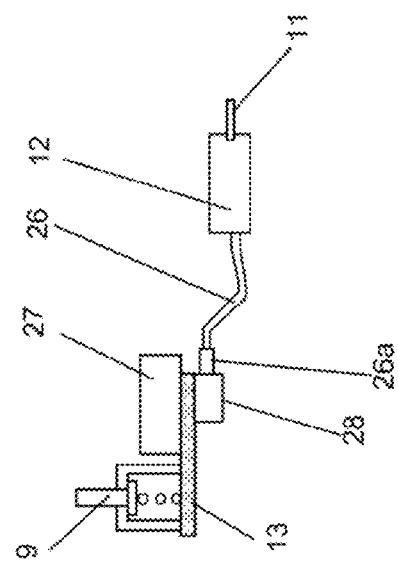
FIG. 9 is a side view of a major part of a carrying case according to yet another modification of the first exemplary embodiment.
Figure 10:
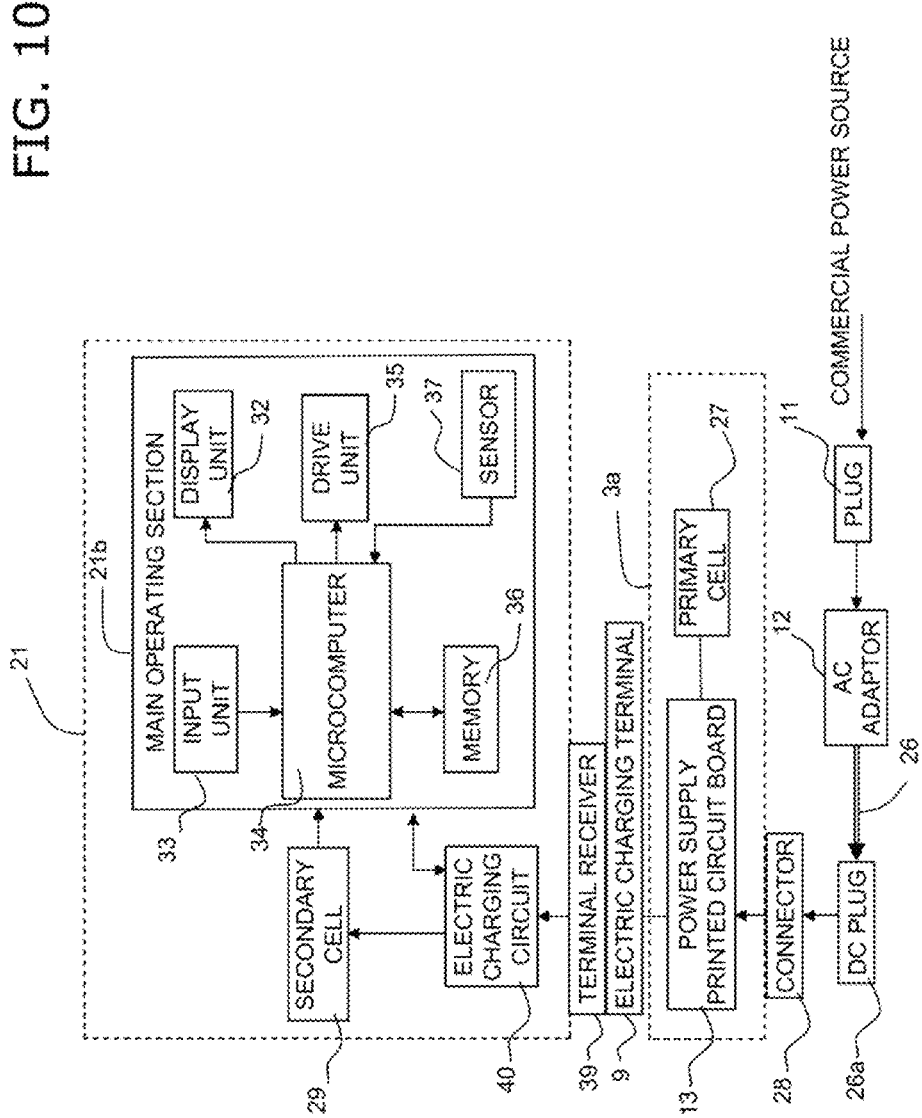
FIG. 10 is a block diagram of a syringe system including the carrying case illustrated in FIG. 9.

Further, as to another exemplary modification of the aforementioned first exemplary embodiment, for instance, the electric charging device 3a of the carrying case 1 may have both the primary battery 27 and the AC adaptor 12, as illustrated in FIGS. 9 and 10. In this case, the power supply printed circuit board 13 includes a switch control unit configured to switch between a power supply from the primary battery 27 and a power supply from the AC adaptor 12. Further, the electric charging device 3a may include a sensor 37 for detecting whether or not the AC adaptor 12 is connected to a power source such as a commercial power source or the like. Therefore, the electric charging device 3a may cause the aforementioned switch control unit to switch between the power supply sources based on an output from the sensor 37 and supply electric power.

The electric charging device 3a may include a plurality of the primary batteries 27. Further, the primary battery 27 may be an alkaline cell or a manganese cell.

With the structure, when a user brings an AC adaptor 12 with him/her, it is possible to electrically charge the pharmaceutical injection device 21 by connecting the AC adaptor 12 to the power source. On the other hand, when a user does not carry an AC adaptor 12 with him/her, it is possible to electrically charge the pharmaceutical injection device 21 using the primary battery 27.

As a result, a user can choose a power supply source depending on his/her situation. It is therefore possible to provide a carrying case that is more user-friendly than well-known carrying cases.

(D)

In the aforementioned first exemplary embodiment, an example in which the carrying case 1 includes an LED 10 has been given. However, the present exemplary embodiment is not limited to this.

For example, the carrying case 1 may have a lamp or any other suitable light source instead of an LED 10.

The structure can also achieve similar advantageous effects as those achieved by the aforementioned exemplary embodiment.

(E)

In the aforementioned first exemplary embodiment, an example in which the carrying case 1 includes an electric charging terminal spring 9a has been given. However, the present exemplary embodiment is not limited to this.

For example, the carrying case 1 may include any suitable elastic member other than the electric charging terminal spring 9a. In other words, any suitable elastic member may be used as long as it can urge the electric charging terminal 9 in a direction that the electric charging terminal 9 protrudes from the main body accommodation portion 6.

The structure can also achieve similar advantageous effects as those achieved by the aforementioned exemplary embodiment.

(F)

A user may carry the carrying case 1 with him/her while putting it in a drawstring bag or the like. Alternatively, a user may carry the carrying case 1 with him/her with a strap attached to the carrying case 1. It is possible to reliably mitigate shocks to the carrying case 1 when a shock-absorbing material is attached to the drawstring bag or the like.

(G)

The carrying case 1 is designed such that the center of gravity is placed at a position separated away from the hinges (20a and 20b) about which the carrying case 1 is opened and closed. Further, the carrying case 1 is designed to have a weight balance between the bottom case 2 and the cover 20 such that the bottom case 2 is heavier than the cover 20. With the structure, the carrying case 1 is allowed to be stably placed without partially floating from or tilting when the cover 20 is opened.

2. Second Embodiment

Figure 11:
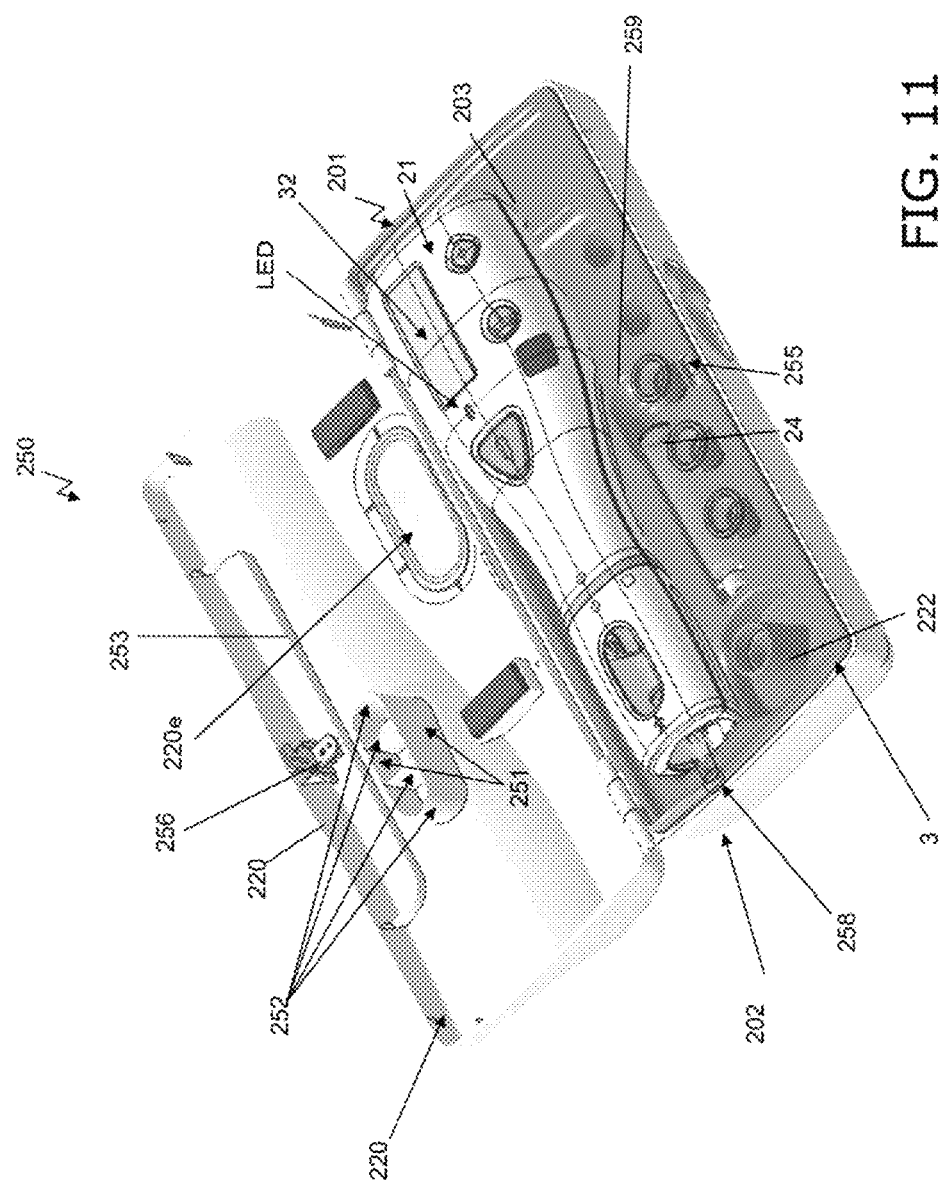
FIG. 11 is a perspective view of an opened state of a carrying case for a syringe system according to a second exemplary embodiment of the present invention.

FIG. 11 illustrates a syringe system 250 including a carrying case 201 and the pharmaceutical injection device 21 according to a second exemplary embodiment of the present invention.

The carrying case 201 of the second exemplary embodiment is characterized in that it includes an open/close detection unit 255 for detecting opening and closing of a cover 220 and has a function of stopping and starting electric charging in conjunction with the opening and closing actions of the cover 220.

It should be noted that the carrying case 201 includes a bottom case 202, a bottom inner case 203 and the cover 220, similarly to the first exemplary embodiment. Explanation of the same components as those in the first exemplary embodiment will be hereinafter omitted.

<2.1 Open/Close Detection Unit>

Figure 12B:
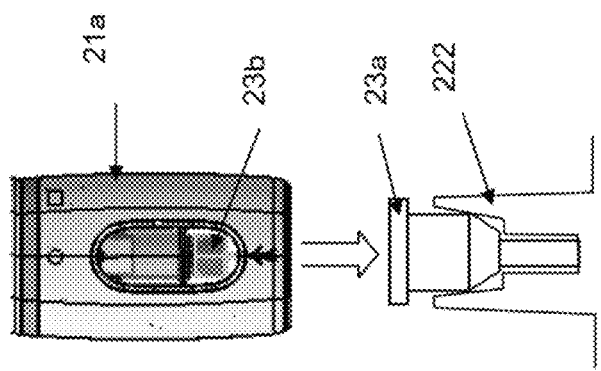
FIG. 12B is a diagram illustrating a usage condition of a protection cap for a needle.
Figure 12A:
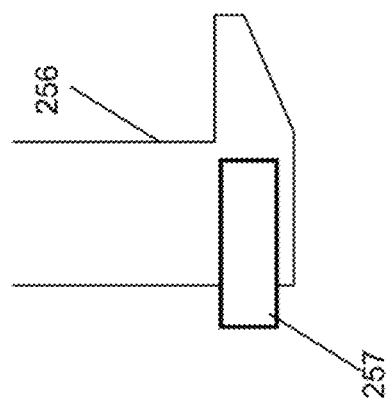
FIG. 12A is a diagram illustrating an engaged state of a lock plate of the carrying case illustrated in FIG. 11.

As illustrated in FIG. 12A, the open/close detection unit 255 for detecting opening and close of the cover 220 includes a detection sensor 257 disposed in the bottom inner case 203. Examples of the detection sensor 257 include a reflective photosensor, a transmissive photosensor and the like. It is also obviously possible to detect opening and closing of the cover 20 using a proximity sensor or a mechanical switch. The detection sensor 257, disposed in the inside of the open/close detection unit 255, detects reflection or transmission of light when the cover 220 is opened or closed using a lock plate 256 disposed in the cover 220. Accordingly, the opening or closing of the cover 220 is determined.

The detection sensor 257 is electrically connected to a power supply printed circuit board of an electric charging device (not illustrated in the figures), which is similar to the first exemplary embodiment. An open/close detection signal of the detection sensor 257 is inputted into the power supply printed circuit board. The power supply printed circuit board then stops or starts electric charging in response to a change of the inputted signal. For example, the power supply printed circuit board stops electric charging in response to an opening of the cover 220 and starts electric charging in response to a closing of the cover 220.

<2.2 Others>

<2.2.1>

Similarly to the first exemplary embodiment, the carrying case 201 of the present exemplary embodiment includes a needle protection cap holding portion 222. The protection cap holding portion 222 will be used as follows.

As illustrated in FIG. 12B, an unused needle is put in the pharmaceutical injection device 21 and a needle protection cap 23a is put on the protection cap holding portion 222. After the pharmaceutical injection device 21 is used, a tip cap 21a that has been detached from the pharmaceutical injection device 21 is pushed from above onto the protection cap 23a put on the protection cap holding portion 222. As a result, a used needle 23b attached to the tip cap 21a is attached to the protection cap 23a. The used needle 23b is then discarded together with the protection cap 23a.

With the structure, the used needle 23b can be safely detached from the pharmaceutical injection device 21 without being exposed to the outside. Further, the structure allows especially a user with a physically disabled hand to discard a needle safely and easily.

<2.2.2>

The carrying case 201 of the present exemplary embodiment includes pharmaceutical presser ribs 251 and 252 in the roughly center part of the inside of the cover 220 for fixing and protecting the pharmaceutical syringe 24 accommodated in the bottom inner case 203.

Figure 13:
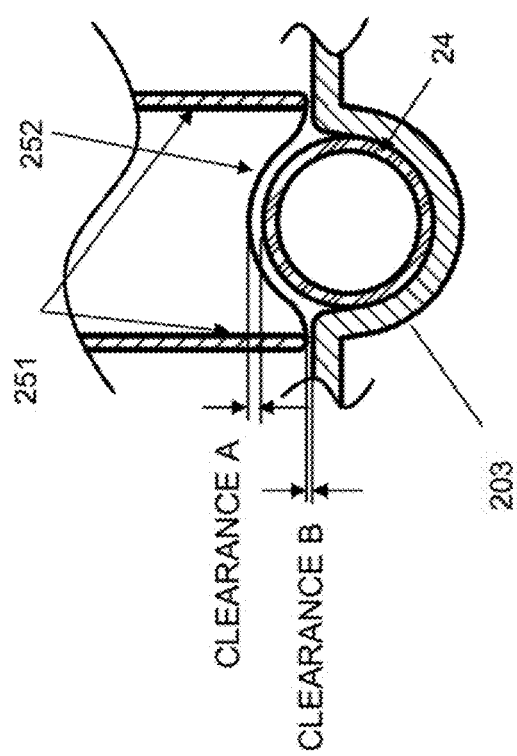
FIG. 13 is a cross-sectional view of a pharmaceutical presser rib when the carrying case illustrated in FIG. 11 is closed.

FIG. 13 illustrates cross-sectional views of the pharmaceutical presser ribs 251 and 252 when the carrying case 201 is in a closed state. A clearance B is formed between the pharmaceutical presser rib 251 and the bottom inner case 203, whereas a clearance A is formed between the pharmaceutical presser rib 252 and the pharmaceutical syringe 24. The clearance A is greater than the clearance B. From this point, when the cover 220 is further pressed from above, the clearance A is still kept between the pharmaceutical presser rib 252 and the pharmaceutical syringe 24. Therefore, load is not applied to the pharmaceutical.

It should be noted that a reference numeral 253 in FIG. 11 indicates an equipment presser. When the carrying case 201 is in a closed state, the equipment presser presses a needle accommodation portion (portions) 30 (see FIG. 1) that an unused needle (or needles) 23 and the like is accommodated.

<2.2.3>

Similarly to the first exemplary embodiment, the carrying case 201 of the present exemplary embodiment includes a window portion 220e. The window portion 220e is disposed in such a position that allows the pharmaceutical injection device 21 accommodated in the carrying case 201 to be visible from the outside while the carrying case 1 is in a closed state. The window portion 220e is made of transparent or translucent plastic or glass, or formed as a cutout. Further, an LED or a display unit 32 of the pharmaceutical injection device 21 can be visually checked through the window portion 220e.

<2.2.4>

The carrying case 201 of the present exemplary embodiment includes an enlarged recess 259 as a space for taking the pharmaceutical syringe out of the accommodation portion for the pharmaceutical syringe 24 in the bottom inner case 203. Pharmaceutical of the enlarged recess 259 allows a user to easily take the pharmaceutical syringe 24 out of the accommodation portion with his/her fingers. Further, the pharmaceutical syringe is accommodated such that its needle attachment side thereof is directed opposite to the enlarged recess 259. Therefore, a user is prevented from touching the needle attachment side of the pharmaceutical syringe when taking out the pharmaceutical syringe for attaching a needle thereto. The needle and the needle attachment portion of the pharmaceutical syringe are thereby prevented from contamination.

<2.2.5>

As illustrated in FIG. 11, the carrying case 201 of the present exemplary embodiment includes a recess 258 in the bottom inner case 203 that allows the pharmaceutical injection device 21 to be accommodated in the carrying case 201 with a protection cap attached to the pharmaceutical injection device 21. The protection cap 23a is further protruded than the tip cap 21a when the pharmaceutical injection device 21 is accommodated in the carrying case 201 with the pharmaceutical syringe 24, the injection needle 23 attached to the pharmaceutical syringe 24, and the protection cap 23a as a needle cover being attached to the pharmaceutical injection device 21. Therefore, the recess 258 is formed to accommodate such protruded part. With the configuration, a user does no longer need to attach the pharmaceutical syringe 24 and the needle with the protection cap 23a to the pharmaceutical injection device 21 when the pharmaceutical is administered, and operability can be thereby enhanced.

<2.3 Features of Second Exemplary Embodiment>

In addition to the aforementioned features of the first exemplary embodiment, the carrying case 201 of the present exemplary embodiment includes the open/close detection unit 255 for detecting opening and closing of the cover 220 and is configured to stop and start electric charging in response to the opening and closing action of the cover 220. Therefore, the carrying case 201 can efficiently execute electric charging.

Further, the carrying case 201 of the present exemplary embodiment includes the protection cap holding portion 222, the pharmaceutical presser ribs 251 and 252, the window portion 220e, the enlarged recess 259 for taking out the pharmaceutical syringe, the recess 258 and the like. Therefore, the carrying case 201 can be a carrying case with superior safety and convenience for the pharmaceutical injection device.

3 Third Exemplary Embodiment

Figure 14:
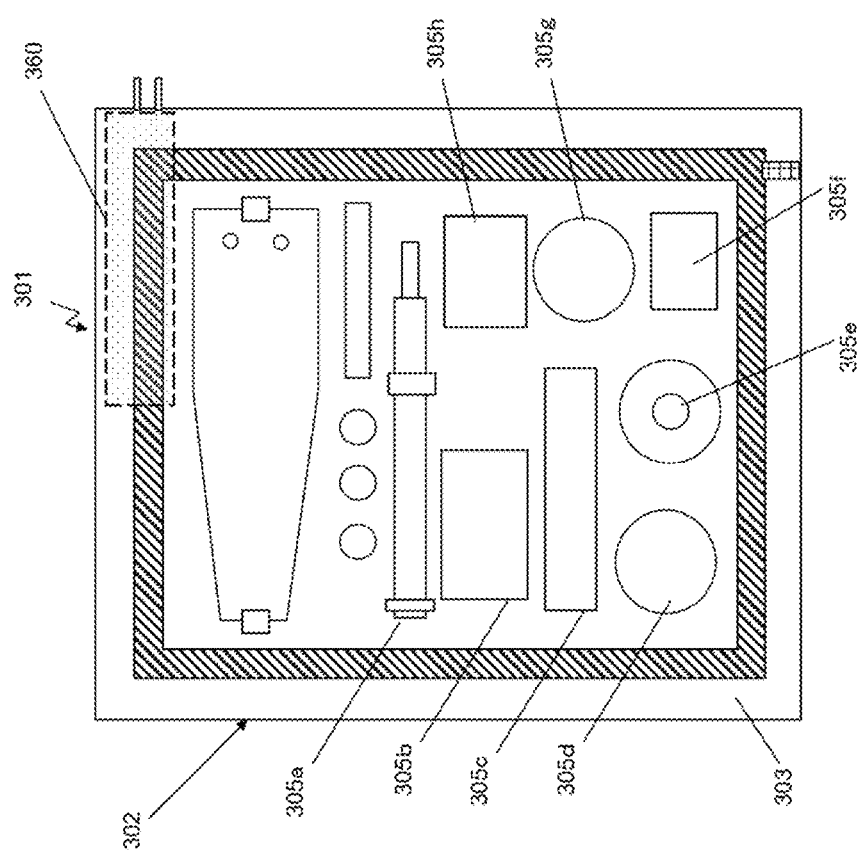
FIG. 14 is a plan view of a bottom case of a carrying case according to a third exemplary embodiment of the present invention.

FIG. 14 is a plan view of a bottom case 302 of a carrying case 301 according to a third exemplary embodiment of the present invention.

The carrying case 301 of the third exemplary embodiment is mainly characterized in that it includes a two-agent mixing portion 305e.

It should be noted that explanation of the components identical to those in the first exemplary embodiment will be hereinafter omitted.

<3.1 Accommodation Portions>

A bottom inner case 303 includes a manual pharmaceutical injection device accommodation portion 305a, a blood glucose meter accommodation portion 305b, a puncture device accommodation portion 305c, a puncture device needle accommodation portion 305d, the two-agent mixing portion 305e, a sterilized absorbent cotton accommodation portion 305f, a blood glucose sensor/blood glucose sensor bottle accommodation portion 305g, a spare battery accommodation portion 305h, and a power source cord accommodation portion 360.

The manual pharmaceutical injection device accommodation portion 305a accommodates, for instance, a manual-type simplified pharmaceutical injection device (not illustrated in the figures), which is different from the pharmaceutical injection device 21 (FIG. 1) according to the present invention. The puncture device accommodation portion 305c accommodates a device for executing a puncture operation with respect to a living body for the purpose of measuring a blood glucose level. The puncture device needle accommodation portion 305d accommodates a needle for the puncture device for measuring a blood glucose level. The two-agent mixing portion 305e includes a protrusion, which will be described later, and mixes two pharmaceutical agents that are separated in the initial state within the syringe. The sterilized absorbent cotton accommodation portion 305f accommodates sterilized absorbent cottons for sterilizing a part of a living body to be injected or punctured. The blood glucose sensor/blood glucose sensor bottle accommodation portion 305g accommodates a sensor to be attached to the blood glucose meter for measuring a blood glucose level and a bottle accommodating the sensor. The spare battery accommodation portion 305h accommodates a replacement battery (a rechargeable battery) for the pharmaceutical injection device 21, a replacement battery (a primary battery) for the blood glucose meter, and the like. The power source cord accommodation portion 360 accommodates an AC cord or the like.

As described above, the carrying case of the third exemplary embodiment is an integrated carrying case that allows a user to execute a series of all operations staring from measurement of a blood glucose level and the like to injection of the pharmaceutical. The integrated structure prevents user's mistakes such as user's forgetting to bring equipment. Additionally, a user can find which equipment is missing by only checking all the equipment pieces accommodated in the carrying case. It is thus possible to prevent both user's forgetting to bring the equipment and missing of any equipment pieces.

<3.2 Two-Agent Mixing Portion>

Figure 15:
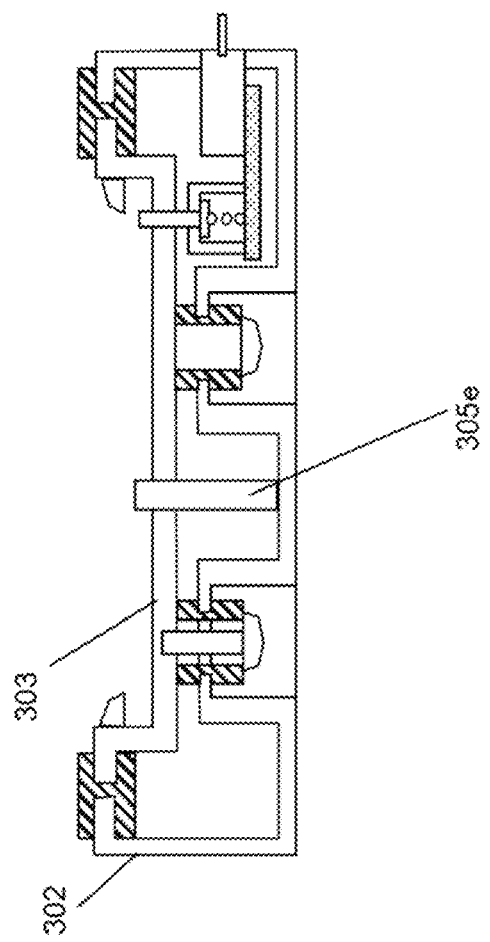
FIG. 15 is a cross-sectional view of the inside of the bottom base illustrated in FIG. 14.

FIG. 15 is a partial cross-sectional view of the bottom case 302 similar to FIG. 3A and illustrates a lateral cross-section of the two-agent mixing portion 305e. FIGS. 16A to 16C are diagrams illustrating operations of the two-agent mixing portion 305e. The pharmaceutical syringe 24 includes a needle portion 24a, a pharmaceutical agent (solid) 24b, a solid containing portion 24c, a liquid containing portion 24d, rubbers R1 and R2, and a flow path portion 24e.

In the initial state as illustrated in FIG. 16A, the solid pharmaceutical agent 24b is contained in the solid containing portion 24c of the pharmaceutical syringe 24 while being separated from a liquid contained in the liquid containing portion 24d by the rubber R1. For using the pharmaceutical syringe 24, as illustrated in FIG. 16B, the bottom end of the pharmaceutical syringe 24 is pressed onto the two-agent mixing portion 305e (downwards in FIG. 16A). The two-agent mixing portion 305e thereby presses the rubber R2 positioned in the vicinity of the bottom end of the pharmaceutical syringe 24. The liquid contained in the liquid containing portion 24d is then pressed upwards. Further, the rubber R1 is also pressed and moved upwards. When the rubbers R2 and R1 are further pressed upwards and reach the position where the flow path portion 24e is disposed, the liquid contained in the liquid containing portion 24d flows into the solid containing portion 24c through the flow path portion 24e. As a result, the solid pharmaceutical agent 24b contained in the solid containing portion 24c starts melting and mix of the pharmaceutical agents is started. When the pharmaceutical syringe 24 is further pressed onto the two-agent mixing portion 305e as illustrated in FIG. 16C, the rubbers R2 and R1 are unitarily moved while being abutted to each other.

As described above, the solid pharmaceutical agent 24b all melts by pressing the pharmaceutical syringe 24 onto the two-agent mixing portion 305e to reach the bottom surface of the two-agent mixing portion 305e. Mixing of two pharmaceutical agents is thus completed.

<3.3 Features of Third Exemplary Embodiment>

The carrying case 301 of the present exemplary embodiments includes the two-agent mixing portion 305e in addition to the aforementioned features of the first and second exemplary embodiments. Accordingly, it is possible to easily mix insulin or the like contained in the pharmaceutical syringe 24.

4. Fourth Exemplary Embodiment

Figure 17:
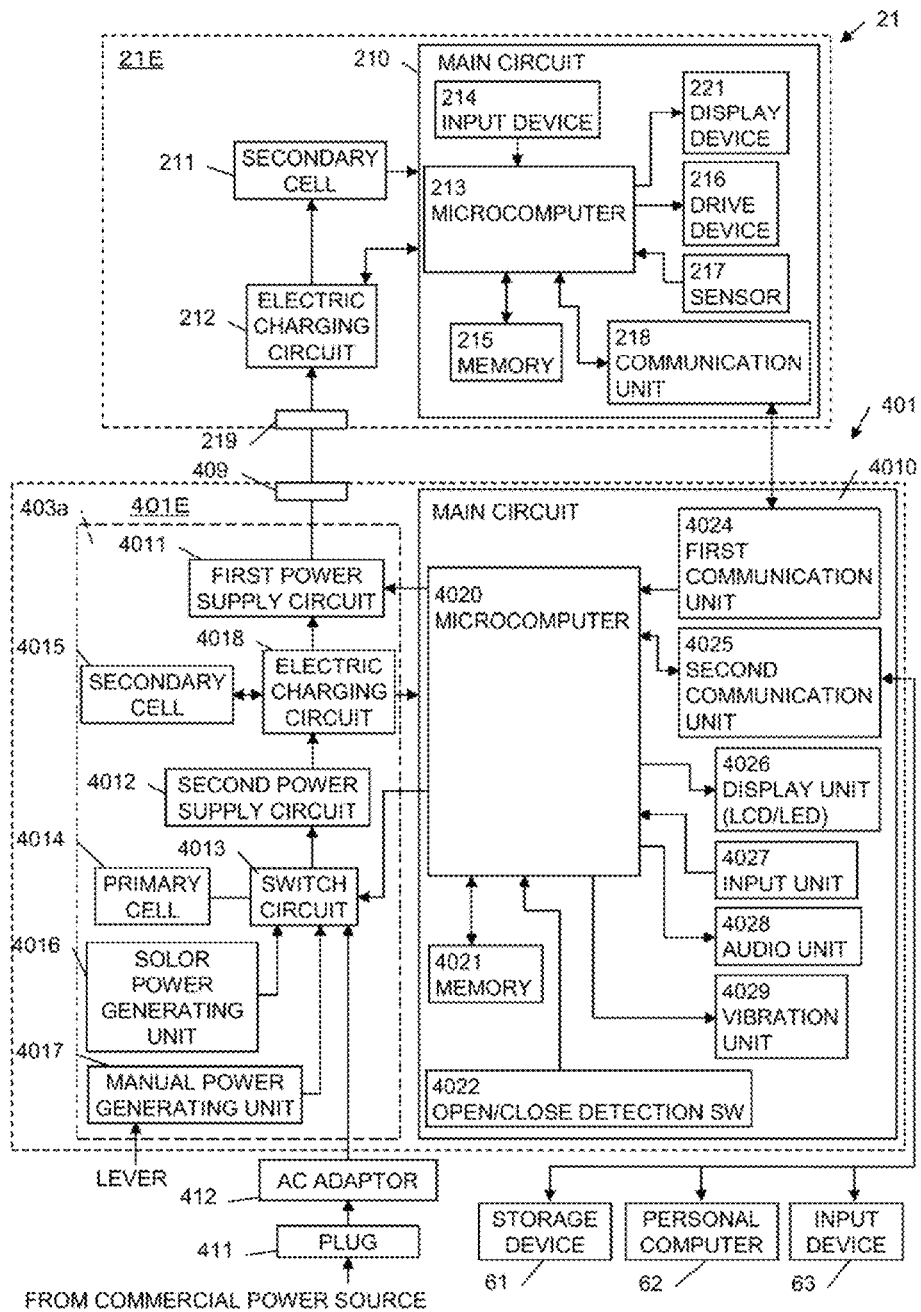
FIG. 17 is a schematic configuration diagram of an electric section of a carrying case and an electric section of a pharmaceutical injection device in a fourth exemplary embodiment of the present invention.

FIG. 17 illustrates an exemplary configuration of an electronic section 401E of a carrying case 401 and an electronic section 21E of the pharmaceutical injection device 21 according to a fourth exemplary embodiment of the present invention. It should be noted that the electronic sections 401E and 21E of the present exemplary embodiment can be also partially or entirely applied to the aforementioned carrying cases 1, 201 and 301 of the first to third exemplary embodiments.

<4.1 The Electronic Section 21E>

The electronic section 21E of the pharmaceutical injection device 21 includes a main circuit 210, a rechargeable battery 211, and an electric charging circuit 212. Electric power is supplied to the electronic section 21E through the carrying case 401, which will be described later.

The rechargeable battery 211 is a rechargeable battery including a nickel hydride battery, a lithium ion battery or the like. The electric charging circuit 212 is a circuit for electrically charging the rechargeable battery. The main circuit 210 is activated with electric power supplied from the rechargeable battery 211. The main circuit 210 includes a microcomputer 213, an input device 214, a memory 215, a drive device 216, a sensor 217, a communication unit 218, an electric charging terminal 219 and a display device 221.

The microcomputer 213 is configured to control a main body of the pharmaceutical injection device 21 based on a written F/W (i.e., firmware). The input device 214 is used when the amount of pharmaceutical injection is changed or an injection action is executed by the main body of the pharmaceutical injection device 21. The memory 215 stores a set injection amount of pharmaceutical agent, a past injection amount of the pharmaceutical agent, the number of injections of the pharmaceutical agent, a time for injection of the pharmaceutical agent and the like. The drive device 216 is mainly formed by a motor and a motor driver. The motor is rotated and a piston is then moved back and forth to administer the pharmaceutical agent into a living body. The drive device 216 further executes needle puncturing and pulling actions of the pharmaceutical injection device 21. The sensor 217 is used for counting a pulse plate (referred to as an encoder) directly connected to the motor and controlling a moving distance during the needle puncturing and pulling actions. The communication unit 218 is configured to execute wired or wireless communication with the carrying case 401 through the electric charging device for transmitting to the carrying case 401 the setting of the injection amount of the pharmaceutical agent, the past injections of the pharmaceutical agent stored in the main body memory, a current remaining battery level and the like. In the wired communication, a USB or the like is used. In the wireless communication, on the other hand, Bluetooth, a wireless LAN or the like is used. The electric charging terminal 219 is electrically connected to an electric charging terminal 409 of an electric charging device 403a of the carrying case 401 by means of either the wired connection (e.g., using a contact-type connection) or the wireless connection (e.g., using an eddy current technique) and is used for supplying electric power to the pharmaceutical device 21 for electric charging. The display device 221 is, for instance, a liquid crystal display configured to display a current status, warning, caution or the like for allowing a user to be aware of it.

<4.2 Electronic Section 401E>

The electronic section 401E of the carrying case 401 includes a main circuit 4010, a first power supply circuit 4011, a second power supply circuit 4012, a switch circuit 4013, a primary battery 4014, a rechargeable battery 4015, a solar power generating unit 4016, and a manual power generating unit 4017.

The electronic section 401E is supplied with electric power by a commercial power source through a plug 411 and an AC adaptor 412. The AC adaptor is a device for converting a household AC power of 100 V or the like into a DC power. The plug 411 is designed to be connected to a household power source (e.g., AC power of 100V).

Further, external devices, including a storage device 61, a personal computer 62, an input device 63, and the like are connected to the electronic section 401E. The storage device 61 is configured to store information in a USB memory, an SD memory and/or the like. The personal computer 62 is used for receiving the injection amount of the pharmaceutical agent and the like through a predetermined communication, storing the received information, and executing computations such as data processing for user's easy understanding. The input device is a USB keyboard and/or the like to be used for directly receiving external data input.

The first power supply circuit 4011 is a circuit for controlling electric power supply to the pharmaceutical injection device 21. The second power supply circuit 4012 is a circuit for controlling electric power supply to an electric charging circuit 4018. The switch circuit 4013 is a circuit for switching among four power sources connected to the switch circuit 4013 (i.e., the primary battery 4014, the solar power generating unit 4016, the manual power generating unit 4017, and a commercial power source). It should be noted that the number of power sources may not be necessarily four and may be greater than or less than four. Further, the switch circuit may not be used when only one power source is mounted.

The primary battery 4014 is a disposal battery such as an alkaline battery or the like. The rechargeable battery 4015 is a chargeable battery such as a nickel hydride battery, a lithium ion battery or the like. It should be noted that attachment of the rechargeable battery 4015 to the carrying case 401 allows a user to execute a variety of operations excluding electric charging such as an operation of the input device 63 mounted in the carrying case 401 and a communication operation even, which will be described later, without an electric power supply from a commercial power source.

The solar power generating unit 4016 is a unit for converting a solar power into electric power using a solar battery or the like. The solar power generating unit 4016 is configured to supply electric power for electric charging of the rechargeable battery or other purposes. Further, the manual power generating unit 4017 is a unit for converting an external force into electric power. For example, the manual power generating unit 4017 is configured to generate electric power by a user rotating a lever with his/her hand. The generated electric power is used for electric charging of the rechargeable battery or other purposes.

The electric charging device 403a includes the aforementioned components, i.e., the first power supply circuit 4011, the second power supply circuit 4012, the switch circuit 4013, the primary battery 4014, the rechargeable battery 4015, the solar power generating unit 4016 and the manual power generating unit 4017.

The main circuit 4010 includes a microcomputer 4020, a memory 4021, a lid open/close detection SW 4022, a first communication unit 4024, a second communication unit 4025, a display unit 4026, an input unit 4027, an audio unit 4028, and a vibration unit 4029.

The microcomputer 4020 is configured to control an electric charging function, a communication function and the like in the carrying case 401. The memory 4021 is disposed in the inside of the carrying case 401. The memory 4021 stores the set injection amount of the pharmaceutical agent, the past injection amount of the pharmaceutical agent and the like. The open/close detection SW (switch) 4022 detects opening and closing of the carrying case 401. When the cover (i.e., a lid) of the carrying case 401 is opened, the first power supply circuit 4011 is shut down for preventing the main body of the pharmaceutical injection device 21 from being electrified and charged. When the cover is closed, electric charging of the rechargeable battery 4015 and data communication between the memory 215 and the memory 4021 may be automatically started.

The first communication unit 4024 is a circuit configured to communicate with the main body of the pharmaceutical injection device 21. The second communication unit 4025 is allowed to communicate with external devices by means of either a wired communication (USB, LAN or the like) or a wireless communication (Bluetooth, wireless LAN or the like). The external devices herein refer to the input device 63, the personal computer 62 and the like.

The display unit 4026 is configured to display the current status, warning, caution or the like for allowing a user to be aware of it. Details of the display contents will be described below. The input unit 4027 includes a button and the like. It should be noted that the input unit 4027 may be connected to the carrying case 401 as an external device. In this case, the input unit 4027 may be a keyboard including ten-keys (i.e., numeric keys) and numeric and alphabetic character keys. Data entry for setting the injection amount of the pharmaceutical agent, mode switching, and mode selection are executed for the pharmaceutical injection device 21 using the input device 63 connected to the second communication unit 4025. In this case, the input device 63 may be integrally provided with the carrying case 401 or may be provided as a separate external component. Further, data entry may be executed using menu keys displayed on the display unit 4026.

Obviously, the carrying case 401 may be configured to communicate with a blood glucose meter by means of a wireless communication and automatically calculate a blood glucose level based on the data received from the blood glucose meter. Further, the blood glucose measurement data may be temporarily stored in the memory provided in the carrying case 401 and may be transmitted to the pharmaceutical injection device 21 through the first communication unit 4024 when the pharmaceutical injection device 21 is connected to the carrying case 401. Subsequently, the injection amount of the pharmaceutical agent may be automatically calculated by the pharmaceutical injection device 21.

The audio unit 4028 is configured to announce a user of the current status, warning, caution or the like (e.g., a remaining available number of times for injection based on the injection amount of the pharmaceutical agent of the pharmaceutical injection device 21) by means of sound produced by a buzzer, a sounder, a speaker or the like.

The vibration unit 4029 is configured to generate vibration/vibrations in the carrying case 401 using a vibrator or the like for informing a user of warning, caution or the like.

<4.3 Features of Fourth Exemplary Embodiment>

The carrying case 401 of the present exemplary embodiment is configured to execute electric charging and communication with the pharmaceutical injection device 21 in addition to the aforementioned features of the first and third exemplary embodiments. Therefore, the carrying case 401 can be a carrying case with superior convenience and safety.

5. Fifth Exemplary Embodiment

The following explanation relates to aspects of the user interface in the carrying case with an electric charging function. It should be noted that the carrying case 401 will be hereinafter exemplified as the carrying case.

<5.1 Display Function>
<5.1.1 Display of Electric Charging Status>

FIG. 18A illustrates operation patterns of an LED (i.e., the display unit 4026 mounted in the carrying case 401) regarding an electric charging status of the carrying case 401. It should be noted that the LED herein used may be of a single-color type or a multi-color type and its blinking period is set to be roughly a second.

FIG. 18B illustrates display patterns of an LCD (i.e., the display unit 4026 mounted in the carrying case 401) regarding the electric charging status of the carrying case 401. It should be noted that the remaining battery level is displayed on an appropriate area of the operation screen in a normal operation, i.e., while the carrying case 401 is not being charged or in a non-charged state, whereas the remaining battery level is not displayed during electric charging or when completion of electric charging is displayed.

It should be noted that the display may be executed by either the LED or the LCD. Further, the LCD may display, as a charging status of the carrying case 401, an available number of injections of the pharmaceutical agent by the pharmaceutical injection device 21 in accordance with the remaining battery level.

<5.1.2 Display of Communication Status>

FIG. 18C illustrates operation patterns of the LED (i.e., the display unit 4026 mounted in the carrying case 401) regarding a communication status of the carrying case 401. It should be noted that the communication status of the carrying case 401 refers to a communication status between the carrying case 401 and a device connected to the carrying case 401 (e.g., a personal computer, an SD card or the like). In FIG. 18C, "unconnected" refers to a status that the carrying case 401 is not connected to any device connectable thereto, whereas "connected" refers to a status that the carrying case 401 is connected to a device connectable thereto. Further, "communicating" refers to a status that the carrying case 401 is connected to and communicated with a device connectable thereto.

FIG. 18D illustrates display patterns of the LCD (i.e., the display unit 4026 mounted in the carrying case 401) regarding the communication status of the carrying case 401.

It should be noted that display may be executed by either the LED or the LCD.

<5.1.3 Display of Electric Conduction>

An LED for an electric conduction display purpose, which is different from the LED for an electric charging display purpose, is lit during connection (electric conduction) of the carrying case 401 to the AC adaptor. It should be noted that the LED may be lit in different colors if the LED is operated in both an electric conduction status and an electric charging status. For example, the LED is lit in green during an "electric conduction" operation. Further, the LED blinks in red during an "electric charging" operation, whereas the LED is lit in red for "completion of electric charging".

Further, the LED displays, for instance, characters indicating "electric charging" or a picture of an "AC line" during electric conduction.

It should be noted that display may be executed by either the LED or the LCD.

<5.2 Audio Guidance Function>

In addition to or instead of the aforementioned display function, the audio unit 4028 (FIG. 17) of the carrying case 401 may be configured to inform a user of "electric charging" and "completion of electric charging" by means of audio guidance.

Further, the audio unit 4028 may be configured to inform a user of a communication status with a connected device, including "connected", "communicating" and "completion of communication" by means of audio guidance.

Further, the audio unit 4028 may be configured to inform a user of warning. For example, the audio unit 4028 may executes an audio guidance such as "charging is unavailable" if electric charging cannot be started due to some sort of trouble, "charging is insufficient" if an insufficiently charged state is detected when the pharmaceutical injection device 21 is set, "set the main body correctly" when the pharmaceutical injection device 21 is not correctly set.

Further, the audio unit 4028 may be configured to inform a user of a time of injection of the pharmaceutical agent. For example, the audio unit 4028 may inform a user of a predetermined clock time set based on a calendar and/or a timer, such as a scheduled injection time and/or a blood glucose level measurement time.

<5.3 Warning Function>

The carrying case 401 may have a warning function using a buzzer or vibration instead of the aforementioned display function or in addition to the aforementioned display function and the aforementioned audio guidance function.

The audio unit 4028 (FIG. 17) may be configured to inform a user of "electric charging" and "completion of electric charging" using a buzzer. In this case, different buzzer sounds may be used for "electric charging" and "completion of electric charging", respectively.

The vibration unit 4029 (FIG. 17) may be configured to inform a user of "electric charging" and "completion of electric charging" by means of vibration. In this case, different vibration patterns may be used for "electric charging" and "completion of electric charging", respectively.

It is preferable that Buzzer or vibration for "completion of electric charging" is set to be more recognizable by a user than that for "electric charging".

<5.4 Lock Function>

The carrying case 401 may have a lock function for preventing it from being used by other users. Examples of the lock function include an electromagnetic lock function, a private code lock function, an authentication lock function or the like.

With the electromagnetic lock function, the carrying case 401 is locked using electromagnets. On the other hand, the carrying case 401 is unlocked by means of a repelling force of the electromagnets.

With the private code lock function, the carrying case 401 is locked using a preliminarily registered password and a personal identification number (numeric numbers). On the other hand, the carrying case 401 is unlocked by inputting the password and the private identification number.

With the authentication lock function, the carrying case 401 is locked using a preliminarily registered fingerprint or voiceprint authentication data of a user. The carrying case 401 is c unlocked through an authentication process by matching a user's fingerprint or voiceprint with the registered data.

<5.5 Features of Fifth Exemplary Embodiment>

In addition to the aforementioned features of the first to fourth exemplary embodiments, the carrying case 401 of the present exemplary embodiment causes the display unit 4026, the audio unit 4028, and the vibration unit 4029 to inform a user of a current status of the carrying case 401 and the pharmaceutical injection device 21, warning, caution or the like. Therefore, the carrying case 401 can be a carrying case with superior safety and convenience.

6 Sixth Exemplary Embodiment

Figure 19:
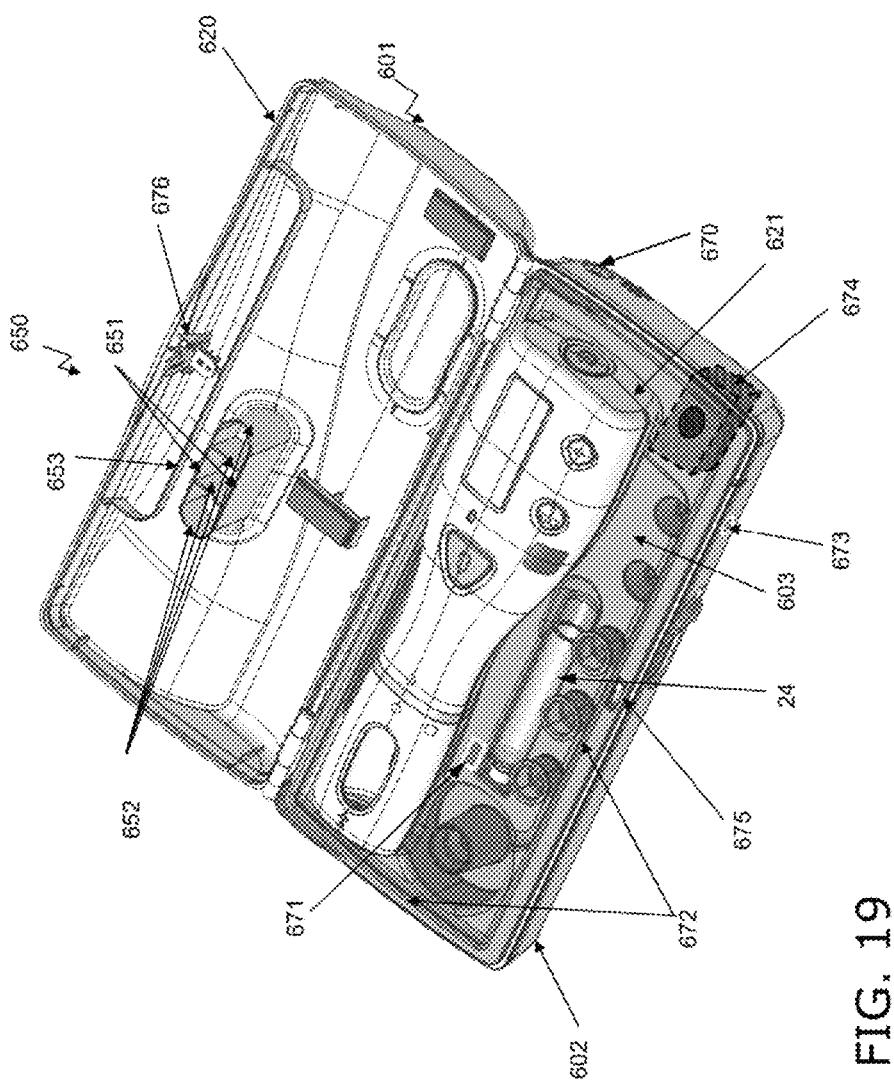
FIG. 19 is a perspective view of an opened state of a carrying case for a syringe system according to a sixth exemplary embodiment of the present invention.

FIG. 19 illustrates a syringe system 650 including a carrying case 601 and the pharmaceutical injection device 21 according to a sixth exemplary embodiment of the present invention.

The carrying case 601 of the sixth exemplary embodiment is characterized in that it has a temperature keeping function of keeping a temperature for preserving the pharmaceutical. Not a few pharmaceuticals to be administered by the pharmaceutical injection device 21 are medicines, such as insulin, that are required to be stored in a cool place. A user normally stores such medicines in a refrigerator or the like. In use, the user takes the pharmaceutical (i.e., in a syringe) out of the cool place, loads the pharmaceutical in a pharmaceutical injection device, and then administers the pharmaceutical to himself/herself. When going out, on the other hand, a user is required to store the pharmaceutical in a separate small cool box filled with ices or the like. This is bothersome for the user. In the present exemplary embodiment, user's convenience is enhanced by providing the carrying case with a temperature keeping function (e.g., low-temperature keeping function).

Similarly to the first exemplary embodiment, the carrying case 601 includes a bottom case 602, a bottom inner case 603, and a cover 620. Similarly to the second exemplary embodiment, the carrying case 601 further includes pharmaceutical presser ribs 651 and 652. As illustrated in FIG. 13, a clearance B is formed between the pharmaceutical presser rib 651 and the bottom inner case 603 whereas a clearance A is formed between the pharmaceutical presser rib 652 and the pharmaceutical syringe 24. The clearance A is greater than the clearance B. From this point, even when the cover 620 is further pressed from above, the clearance A is still kept between the pharmaceutical presser rib 652 and the pharmaceutical syringe 24. Therefore, load is not applied to the pharmaceutical.

A reference numeral 653 indicates an equipment presser. The equipment presser 653 is configured to press the pharmaceutical syringe 24 when the carrying case 601 is in a closed state.

It should be noted that explanation of the same structure as those in the first and second exemplary embodiments will be hereinafter omitted.

<6.1 Temperature Keeping Function>
<6.1.1 Configuration>

The following relates to explanation of the structure for executing a temperature keeping function of the carrying case 601 according to the present exemplary embodiment.

The carrying case 601 includes a power input unit 670, a sealing member 672, a temperature sensor 671, a cooling state display LED 673, a cooling unit (exemplifying a temperature regulation unit) 674, a lock plate 676, and a lock plate engaging portion 675.

The power input unit 670 inputs electric power therein from an external DC power source or an external AC power source. The inputted electric power is used for causing the cooling unit 674 to cool the pharmaceutical in the pharmaceutical syringe 24, as well as for electrically charging the pharmaceutical injection device 21.

The temperature sensor 671 is formed by a thermister or the like and measures a temperature in the carrying case 601 in which the pharmaceutical syringe 24 containing a pharmaceutical is accommodated. The temperature sensor 671 is disposed in the vicinity of the pharmaceutical syringe because the temperature of the pharmaceutical makes a difference. The number of the temperature sensor 671 disposed herein is not limited to one and may be more than one. For example, two temperature sensors may be disposed in the vicinity of the pharmaceutical syringe 24. In this case, it is even possible to enhance reliability by comparing and monitoring temperature data of the both temperature sensors. Further, a temperature sensor may be disposed on an outer surface of the carrying case 601. In this case, it is even possible to regulate a cooling level through the control of the cooling unit 674 based on two types of temperature data from the inner temperature sensor and the outer temperature sensor.

The sealing member 672 seals the carrying case 601. The cooling state display LED 673 displays a cooling state in the inside of the carrying case 601 using a plurality of colors.

The cooling unit 674 is a unit configured to cool the pharmaceutical syringe 24. The cooling unit 674 includes a cooling execution section, a cooling fan, a cooling control section and the like. The cooling execution section is configured to execute cooling with use of normally a Peltier device or the like. The cooling fan supplies a cooling air. The cooling control section is configured to control the cooling execution section for obtaining an appropriate temperature with reference to the temperature measurement data from the temperature sensor 671.

When the cover 620 of the carrying case 601 is closed, the lock plate 676 and the lock plate engaging portion 675 are engaged with each other. The opening and closing of the cover 620 is detected by an open/close detection unit (not illustrated in the figures) having a roughly similar configuration as that of the open/close detection unit 255 (see FIG. 12A) of the second exemplary embodiment. Simply put, the opening and closing of the cover 620 can be detected similarly to the second exemplary embodiment by providing the lock plate engaging portion 674 with a detection unit corresponding to the detection sensor 257 of the second exemplary embodiment. The cooling unit 674 is activated or deactivated based on a signal from the open/close detection unit.

The cover 620, the bottom case 602 and the bottom inner case 603 are preferably made of materials with high thermal insulation properties and high sealing properties or are processed with surface finishing by attaching sealing members to the surfaces thereof in order to enhance a temperature keeping function. Further, a rubber member, such as silicon or urethane, with a high sealing property may be separately formed on the outer periphery of the cover 620.

<6.1.2 Actions>

When the carrying case 601 is electrified from an external power source connected thereto through the power input unit 670, the inside of the carrying case 601 is cooled by the cooling unit at a constant temperature while the temperature within the carrying case 601 is detected by the temperature sensor 671. When a user carries the carrying case 601 with him/her, the carrying case 601 made of a thermal insulation material or the like keeps its inner temperature constant (at a low temperature in this case) for a predetermined term. Further, when a user is in a car, a car battery adaptor may be used for cooling the inside of the carrying case 601 to utilize a car battery. The user's activity area can be thereby expanded and user's comfortableness can be enhanced in his/her daily life.

Further, the lock plate 676 and a lock plate engaging portion 675 of the carrying case 601 detect a closed state of the cover 620 and the cooling unit is automatically activated in response to the detection. The cooling control section of the cooling unit 674 may calculate a difference between the temperature data of the temperature sensor 671 and a preliminarily set cooling temperature and may execute cooling of the pharmaceutical syringe 24 by controlling a cooling level (rapid cooling, strong cooling, intermediate cooling, weak cooling and the like) depending on the temperature difference. When an opened state of the cover 620 is detected, on the other hand, the cooling unit 674 can be deactivated in response to the detection. A user may be informed of the opened state by means of a buzzer or the like.

<6.1.3 Cooling State Informing Function>

The cooling state display LED 673 is configured to display a current temperature state within the carrying case 601. For example, the following display patterns are available.

(1) Green LED lighting: this indicates a cooling state in which cooling is being executed or a predetermined temperature is being kept (i.e., a state that electric power is being supplied to the power source input unit from an external power source).

(2) Yellow LED lighting: this indicates a cooled state in which a low temperature is being kept (i.e., a state that electric power is not being supplied to the power source input unit from an external power source). In this case, a user can determine that the inner temperature is in a necessary predetermined temperature range. It should be noted that yellow LED lighting can be achieved by simultaneously lighting green and red.

(3) Red LED lighting: this indicates a state in which the inner temperature has exceeded a predetermined temperature and cooling is required through a supply of electric power from an external power source.

(4) Red LED blinking: this indicates a state in which the inner temperature has been continuously at temperatures exceeding a predetermined temperature for a predetermined period of time or more and the pharmaceutical condition is required to be checked due to possibility of chemical reactions of the pharmaceutical.

The LED may be configured to regulate the timing of the warning display based on not only the temperature within the carrying case 601 but also the temperature data of the outside of the carrying case measured by a temperature sensor additionally provided to the outer part of the carrying case 601. For example, warning timings may be different between a case that a temperature difference between the outside temperature and the inside temperature is 10 degrees Celsius and a case that the temperature difference is 20 degrees Celsius. Specifically, when the temperature difference is 20 degrees Celsius or more, warning is informed (i.e., LED is lit in red) earlier than the case that the temperature difference is 10 degrees Celsius. Further, the aforementioned required predetermined temperature range may be automatically changed in accordance with the temperature difference in informing a user of warning.

It should be noted that warning may be given by the display unit (e.g., LCD) or the audio unit (FIG. 17) of the carrying case 601 in addition to or instead of the warning by the cooling state display LED 673.

<6.2 Features of Sixth Exemplary Embodiment>

The carrying case 601 of the present exemplary embodiment includes the cooling unit 674 in addition to the aforementioned features of the first to fifth exemplary embodiments. This allows a user to carry a spare pharmaceutical at ease with him/her. Therefore, the carrying case 601 can be a carrying case with superior convenience and safety.

Further, the carrying case 601 of the present exemplary embodiment is configured to cause the display unit (e.g., LED or LCD) or the audio unit to inform a user of the temperature state in the inside of the carrying case 601. This allows a user to take care of the pharmaceutical more accurately and safety of the pharmaceutical can be thereby enhanced.

7. Other Exemplary Embodiments

Exemplary embodiments of the present invention have been explained above. However, the present invention is not limited to the aforementioned exemplary embodiments, and a variety of changes can be made for the aforementioned embodiments without departing from the scope of the present invention. For example, the present invention covers any carrying cases produced by combining all or parts of the aforementioned structures of the first to sixth exemplary embodiments.

Other exemplary embodiments, excluding the aforementioned exemplary embodiments, will be hereinafter explained. However, explanation of the same parts as those in the aforementioned exemplary embodiments will be hereinafter omitted.

7.1 Antibacterial Processing

The antibacterial processing may be executed for the surfaces (including both of the outer and inner surfaces) of the cover and the bottom case of the carrying case of the aforementioned exemplary embodiments.

The antibacterial processing has been widely applied for kitchenware (e.g., cutting boards and kitchen knives) or the like. A normally used technique is antibacterial printing for coating the surfaces. Other than the above technique, the technique of thermally solidifying antibacterial agent may be used.

Execution of the aforementioned antibacterial processing prevents contamination due to attached substances such as blood and enhances easiness of cleaning off such attached substances.

In addition to the aforementioned antibacterial processing, the carrying case may further include a step, a liquid relief portion or a double-walled structure in the opening and closing part of the cover in order to block attached substances (e.g., liquid) from entering the inside of the carrying case. Accordingly, substances such as blood are prevented from attaching to the surface and are also prevented from entering the inside of the carrying case. The carrying case enhances its sanitation and safety.

7.2 Configuration Examples of Carrying Case

FIGS. 20 to 29 illustrate examples of a configuration of the carrying case of the present invention.

7.2.1 Configuration Example 1

FIG. 20 illustrates one example of a configuration of the carrying case in which the carrying case is a horizontal type. FIG. 20A illustrates a top view of a carrying case 701. FIGS. 20B and 20C illustrate a longitudinal cross-sectional view and a transverse cross-sectional view of the carrying case 701 respectively. The carrying case 701 is not provided with a cover and an equipment accommodation portion. Seen from above, a bottom case 702 includes a constriction portion 781. As illustrated in FIG. 20B, a recess 782 is formed in a part of the constriction portion 781. The shape allows a user to easily put/remove the pharmaceutical injection device 21 in/from the bottom case 702.

As illustrated in FIG. 20B, the carrying case 701 allows the pharmaceutical injection device 21 to be put in the bottom case 702. In this state, lock arms 707 and 708, respectively disposed on the ends of the bottom case 702, are engaged with the both ends of the pharmaceutical injection device 21. The pharmaceutical injection device 21 is thereby fixed to the bottom case 702 while an electric charging terminal of the electric charging device 703a and a terminal receiver of the pharmaceutical injection device 21 reliably make contact with each other.

As illustrated in FIG. 20A, the carrying case 701 further includes an LED 710 disposed on the top surface of the bottom case 702 and the electric charging device 703a disposed in the inside of the bottom case 702. The LED 710 and the electric charging device 703a have the same structure and function as those of the corresponding components in the aforementioned first to sixth exemplary embodiments.

As illustrated in FIGS. 20B and 20C, the bottom case 702 further includes elevated protector portions 783 and 784 on the both ends thereof. The tip of the pharmaceutical injection device 21 and a power button 21c disposed on the rear end of the pharmaceutical injection device 21 are prevented from being exposed to the outside and are thereby protected.

7.2.2 Configuration Example 2

FIG. 21 illustrates another example of a configuration of the carrying case in which the carrying case is a horizontal type. FIG. 21A illustrates a top view of a carrying case 801. FIGS. 21B and 21C illustrate a longitudinal side view and a transverse side view of the carrying case 801, respectively. The carrying case 801 does not include an equipment accommodation portion. Further, the carrying case 801 includes a transparent or translucent tip protector portion 885 in place of a cover.

As illustrated in FIG. 21B, the carrying case 801 allows the pharmaceutical injection device 21 to be put in a bottom case 802. When the pharmaceutical injection device 21 is put in the bottom case 802, the pharmaceutical injection device 21 is inserted at an angle with respect to the bottom case 802 while the tip thereof is inserted into the tip protector portion 885, and is then placed in the bottom case 802. The lock arm 708, disposed in the rear end (opposite to the tip protector portion 885) of the bottom case 802, is engaged with the rear end of the pharmaceutical injection device 21. The pharmaceutical injection device 21 is thereby held in the bottom case 802. This allows an electric charging terminal of the electric charging device 803a and a terminal receiver of the pharmaceutical injection device 21 to reliably make contact with each other.

As illustrated in FIG. 21A, the carrying case 801 further includes an LED 810 and the electric charging device 803a. The LED 810 is disposed on the top surface of the bottom case 802 whereas the electric charging device 803a is disposed in the inside of the bottom case 802. The LED 810 and the electric charging device 803a have the same structure and function as those of the corresponding components in the aforementioned first to sixth exemplary embodiment.

As illustrated in FIG. 21C, the bottom case 802 further includes an elevated protector portion 884 on the rear end thereof. The tip protector portion 885 and the protector portion 884 protect the pharmaceutical injection device 21 for preventing its front end and its rear end having the power button 21c from being exposed to the outside.

7.2.3 Configuration Example 3

FIG. 22 illustrates one example of a configuration of the carrying case in which the carrying case is a vertical type. FIG. 22A illustrates a top view of a carrying case 901. FIGS. 9B and 9C illustrate a front view and a side view of the carrying case 901, respectively. The carrying case 901 includes a bottom case 902 and a vertical cover 986. The bottom case 902 allows the pharmaceutical injection device 21 to be held thereto while supporting the rear end of the pharmaceutical injection device 21. The vertical cover 986 is disposed vertically along the main body of the pharmaceutical injection device 21 mounted upright on the bottom case 902.

The carrying case 901 further includes an LED 910 and an electric charging device 903a. The LED 910 is disposed on the top surface of the bottom case 902 as illustrated in FIG. 22A, whereas the electric charging device 903a is disposed in the inside of the bottom case 902 as illustrated in FIG. 22B. The LED 910 and the electric charging device 903a have the same structure and function as those of the corresponding components in the first to sixth exemplary embodiments.

As illustrated in FIG. 22B, electric charging terminals 919 of the pharmaceutical injection device 21 and electric charging terminals 909 of the electric charging device 903a make contact with each other when the pharmaceutical injection device 21 is set in the bottom case 902, and electric charging will be thereby available.

As illustrated in FIGS. 22A and 22C, the vertical cover 986 of the carrying case 901 includes a tip protector portion 983 for covering the tip of the pharmaceutical injection device 21 mounted in the carrying case 901. As illustrated in FIG. 22C, the vertical cover 986 further includes equipment accommodation portions 905 for accommodating the pharmaceutical 24, a needle and the like.

7.2.4 Configuration Example 4

FIG. 23 illustrates another example of a configuration of the carrying case in which the carrying case is a vertical type. FIG. 23A illustrates a top view of a carrying case 1001. FIGS. 23B and 23C illustrate a front view and a side view of the carrying case 1001, respectively. Similarly to the aforementioned configuration example 3, the carrying case 1001 includes a bottom case 1002 and a vertical cover 1086. The bottom case 102 allows the pharmaceutical injection device 21 to be held therein while supporting the rear end of the pharmaceutical injection device 21. The vertical cover 1086 is integrally disposed vertically along the main body of the pharmaceutical injection device 21 mounted upright on the bottom case 1002.

As illustrated in FIG. 23C, the carrying case 1001 further includes an LED 1010 and an electric charging device 1003a. The LED 1010 is disposed on a side surface of the bottom case 1002, whereas the electric charging device 1003a is disposed in the inside of the bottom case 1002. The LED 1010 and the electric charging device 1003a have the same structure and function as those of the corresponding components in the aforementioned first to sixth exemplary embodiments. Similarly to the aforementioned configuration example 3, the electric charging terminal of the pharmaceutical injection device 21 and an electric charging terminal of the electric charging device 1003a make contact with each other, and electric charging will be thereby available.

As illustrated in FIGS. 23A and 23C, the vertical cover 1086 of the carrying case 1001 includes a tip protector portion 1083 for covering the tip of the pharmaceutical injection device 21 mounted in the carrying case 1001.

7.2.5 Configuration Example 5

FIG. 24 illustrates yet another example of a configuration of the carrying case in which the carrying case is a vertical type. FIG. 24A illustrates a top view of a carrying case 1101. FIGS. 24B and 24C illustrate a front view and a side view of the carrying case 1101, respectively. The carrying case 1101 includes a bottom case 1102 and a cover 1120. The bottom case 1102 allows the pharmaceutical injection device 21 to be held therein while supporting the rear end of the pharmaceutical injection device 21. The cover 1120 is detachably mounted on the bottom case 1102 while entirely covering the pharmaceutical injection device 21. The cover 1120 is made of transparent or translucent material.

As illustrated in FIG. 24C, the carrying case 1101 further includes an LED 1110 and an electric charging device 1103a.

The LED 1110 is disposed on a side surface of the bottom case 1102, whereas the electric charging device 1103*a* is disposed in the inside of the bottom case 1102. The LED 1110 and the electric charging device 1103*a* have the same structure and function as those of the corresponding components in the aforementioned first to sixth exemplary embodiments. Similarly to the aforementioned configuration example 3, the electric charging terminal of the pharmaceutical injection device 21 and an electric charging terminal of the electric charging device 1003*a* make contact with each other, and electric charging will be thereby available.

7.2.6 Configuration Example 6

FIG. 25 illustrates yet another example of a configuration of the carrying case in which the carrying case is a horizontal type. FIG. 25A illustrates a top view of a carrying case 1201. FIGS. 25B and 25C illustrate a longitudinal side view and a transverse side view of the carrying case 1201, respectively. The carrying case 1201 does not include an equipment accommodation portion but includes a tip protector portion 1285 shaped for covering roughly half the front part of the pharmaceutical injection device 21 mounted therein.

As illustrated in FIG. 25B, the carrying case 1201 allows the pharmaceutical injection device 21 to be disposed in a bottom case 1202. For putting the pharmaceutical injection device 21 in the bottom case 1202, the pharmaceutical injection device 21 is inserted at an angle with respect to the bottom case 1202 while the tip thereof is inserted into the tip protector portion 1285, and is then placed in the bottom case 1202. A lock arm 1208, disposed in the rear end (opposite to the tip protector portion 1285) of the bottom case 1202, is engaged with the rear end of the pharmaceutical injection device 21. The pharmaceutical injection device 21 is thereby held in the bottom case 1202. This allows an electric charging terminal of an electric charging device 1203*a* and the terminal receiver of the pharmaceutical injection device 21 to reliably make contact with each other.

As illustrated in FIGS. 25A and 25B, the carrying case 1201 further includes an LED 1210 and the electric charging device 1203*a*. The LED 1210 is disposed at the tip protector portion 1285, whereas the electric charging device 1203*a* is disposed in the inside of the bottom case 1202. The LED 1210 and the electric charging device 1203*a* have the same structure and function as those of the corresponding components in the first to sixth exemplary embodiments.

As illustrated in FIG. 25B, the bottom case 1202 further includes an elevated protector portion 1284 on the rear end thereof. The tip protector portion 1285 and the protector portion 1284 protect the pharmaceutical injection device 21 for preventing its front end and its rear end having a power button 21*c* from being exposed to the outside.

7.2.7 Configuration Example 7

FIG. 26 also illustrates yet another example of a configuration of the carrying case in which the carrying case is a horizontal type. FIG. 26A illustrates a top view of a carrying case 1301. FIGS. 26B and 26C illustrate a longitudinal side view and a transverse side view of the carrying case 1301, respectively. The carrying case 1301 is different from the carrying cases of the aforementioned first to sixth exemplary embodiments mainly in that a cover 1320 is made of transparent or translucent material. As illustrated in FIG. 26C, the cover 1320 and a bottom case 1302 are configured to be openable and closable by being coupled to each other by means of a hinge 1387.

As illustrated in FIGS. 26A and 26B, the carrying case 1301 includes an LED 1310 and an electric charging device 1303*a*. The LED 1310 is disposed in a bottom inner case, whereas the electric charging device 1303*a* is disposed in the inside of the bottom case 1302. The LED 1310 and the electric charging device 1303*a* have the same structure and function as those of the corresponding components in the aforementioned first to sixth exemplary embodiments. The bottom inner case includes equipment accommodation portions 1305 and a protection cap holding portion 1322 in predetermined positions.

As illustrated in FIG. 26B, the carrying case 1301 allows the pharmaceutical injection device 21 to be held in the bottom case 1302. In this state, lock arms 1307 and 1308, disposed in the both ends of the bottom case 1302, are engaged with the both ends of the pharmaceutical injection device 21. The pharmaceutical injection device 21 is thereby held in the bottom case 1302. This allows an electric charging terminal of the electric charging device 1303*a* and the terminal receiver of the pharmaceutical injection device 21 to reliably make contact with each other.

FIG. 27 also illustrates another example of a configuration of the carrying case in which the carrying case is a horizontal type similar to the configuration example illustrated in FIG. 26. However, the carrying case is entirely made compact by putting the equipment accommodation portions 1305 in close positions.

FIG. 28 also illustrates another example of a configuration of the carrying case in which the carrying case is a horizontal type similar to the configuration example illustrated in FIG. 26. However, the configuration example of FIG. 28 is different from that of FIG. 26 in that: the cover 1320 is not made of transparent or translucent material; a check window portion 1390 is disposed in the cover 1320; and a pivotable support plate 1388 is disposed in the cover 1320 as illustrated in FIG. 28D. The check window 1390, which is transparent or translucent, is disposed in a position corresponding to a display unit (LED, LCD or the like) of the pharmaceutical injection device 21 when the pharmaceutical injection device 21 is mounted in the carrying case. The support plate 1388 is configured to pivot about a part of the bottom case 1302. A stopper (not illustrated in the figure) acts on the support plate 1388 when the support plate 1388 is opened to a predetermined angle. With the support plate 1388, the carrying case 1301 can be placed in such a manner that the carrying case 1301 slants at a predetermined angle with respect to the horizontal plane. This allows a user to easily watch the check window portion 1390 and the display unit (LED, LCD or the like) of the pharmaceutical injection device 21 while the carrying case 1302 is put on a horizontal plane.

7.2.8 Configuration Example 8

FIG. 29 also illustrates yet another example of a configuration of the carrying case in which the carrying case is a horizontal type. FIG. 29A illustrates a top view of a carrying case 1401. FIGS. 29B and 29C illustrate a longitudinal side view and a transverse side view of the carrying case 1401, respectively. The carrying case 1401 includes a tip protector cover 1489 in place of a cover. The tip protector cover 1489, which is made of transparent or translucent material, is attached to a bottom case 1402 in an openable and closable manner and covers the tip of the pharmaceutical injection device 21.

When the pharmaceutical injection device 21 is mounted in a carrying case 1401, the tip protector cover 1489 is opened and the pharmaceutical injection device 21 is put in the bottom case 1402, as illustrated in FIG. 29B. As illustrated in FIG. 29B, a lock arm 1408, which is disposed in the rear end of the bottom case 1402, is engaged with the rear end of the pharmaceutical injection device 21. The pharmaceutical injection device 21 is thereby held in the bottom case 1402. This allows an electric charging terminal of an electric charging device 1403a and the terminal receiver of the pharmaceutical injection device 21 to reliably make contact with each other.

As illustrated in FIG. 29A, the carrying case 1401 further includes an LED 1410 and the electric charging device 1403a. The LED 1410 is disposed on the top surface of the bottom case 1402, whereas the electric charging device 1403a is disposed in the inside of the bottom case 1402. The LED 1410 and the electric charging device 1403a have the same structure and function as those of the corresponding components in the aforementioned first to sixth exemplary embodiments. The bottom case 1402 includes equipment accommodation portions 1405 in predetermined positions.

In the present configuration example, the bottom case 1402 further includes a wedge bottom portion 1490 with a triangular cross-section as illustrated in FIG. 29C. In this case, the pharmaceutical injection device 21 slants at a predetermined angle with respect to a horizontal plane when accommodated in the carrying case as illustrated in FIG. 29 C. This allows a user to easily watch the display unit (LED, LCD or the like) of the pharmaceutical injection device 21 while the carrying case 1402 is placed on a horizontal plane.

INDUSTRIAL APPLICABILITY

According to the carrying case of the present invention, a user is not required to separately carry an electric charging device with him/her, and the pharmaceutical injection device and a variety of equipment can be protected from shocks due to falling, contact or the like. Therefore, the carrying case of the present invention is especially useful as a carrying case that an older/physically-disabled person carries with him/her when going out.

REFERENCE SIGNS LIST

1 Carrying case
2 Bottom case (Case unit)
2a Support shaft insertion portion
2b Clearance
3 Bottom inner case (Inner case)
3a Electric charging device
4 Shock-absorbing material
5 Equipment accommodation portion
6 Main body accommodation portion (Recess)
7 Lock arm (Lock mechanism)
8 Lock arm (Lock mechanism)
9 Electric charging terminal
9a Electric charging terminal spring (Elastic member)
10 LED (Light source)
11 Plug
12 AC adaptor
13 Power supply printed circuit board
13a Connector
14 Shock-absorbing material
15 Collar
16 Screw
17 Electric charging unit
18 Screw
19 Shock-absorbing material (Second shock-absorbing material)
20 Cover (case unit)
20a Support shaft holding portion
20b Support shaft
20c Equipment presser rib
20d Shock-absorbing material (First shock-absorbing material)
20e Window portion
21 Pharmaceutical injection device
21b Main operating section
22 Protection cap holding portion (Equipment holding portion)
23 Unused needle
24 Pharmaceutical syringe
25 Slide knob (engaging mechanism)
26 Cord
26a DC plug
27 Primary battery
28 Jack (connector)
29 Rechargeable battery
30 Needle accommodation portion
31 Pharmaceutical accommodation portion
32 Display unit
33 Input unit
34 Microcomputer
35 Drive unit
36 Memory
37 Sensor
39 Terminal receiver
40 Electric charging circuit
50 Syringe system

The invention claimed is:

1. A carrying case that accommodates a pharmaceutical injection device for administering a pharmaceutical to a living body, comprising:
   a case unit configured to accommodate the pharmaceutical injection device therein; and
   a temperature regulation unit configured to regulate a temperature within the case unit,
   wherein the temperature regulation unit includes: a cooling execution section configured to execute a cooling operation; a cooling fan configured to supply a cool air into the case unit; and a cooling control section configured to control the cooling execution section.

2. The carrying case according to claim 1,
   wherein the case unit further includes at least one temperature sensor, and
   the cooling control section of the temperature regulation unit is configured to control the cooling execution section based on a value/values measured by the at least one temperature sensor.

3. The carrying case according to claim 1, further comprising:
   an electric charging device mounted in the case unit, the electric charging device including an electric charging terminal electrically connectable to the pharmaceutical injection device, the electric charging device being configured to electrically charge the pharmaceutical injection device,
   wherein the temperature regulation unit is configured to be operated by electric power supplied from the electric charging device.

4. The carrying case according to claim 1,
wherein the case unit includes an openable/closable pair of a cover and a bottom case, and
the temperature regulation unit is configured to stop or start a cooling operation in conjunction with an opening action or a closing action of the cover and the bottom case.

5. The carrying case according to claim 1, wherein the case unit is made of a material having either a thermal insulation property or a sealing property.

6. The carrying case according to claim 1, wherein the case unit has a sealing member attached on an outer surface thereof.

7. The carrying case according to claim 1, further comprising:
a display unit configured to display a temperature status in the inside of the case unit.

8. The carrying case according to claim 1,
wherein the case unit includes an inner case, and
the case unit further includes a third shock-absorbing member between the case unit and the inner case.

9. The carrying case according to claim 1, wherein the case unit is antibacterial.

10. A syringe system, comprising:
the carrying case according to claim 1; and
the pharmaceutical injection device configured to be accommodated in the carrying case.

* * * * *